(12) United States Patent
Holton

(10) Patent No.: US 6,660,866 B2
(45) Date of Patent: Dec. 9, 2003

(54) C10 CARBONATE SUBSTITUTED TAXANES

(75) Inventor: Robert A. Holton, Tallahassee, FL (US)

(73) Assignee: PSU Research Foundation, Inc., Tallahassee, FL (US)

( * ) Notice: Subject to any disclaimer, the term of this patent is extended or adjusted under 35 U.S.C. 154(b) by 94 days.

(21) Appl. No.: 09/776,274

(22) Filed: Feb. 2, 2001

(65) Prior Publication Data

US 2003/0114493 A1 Jun. 19, 2003

Related U.S. Application Data

(60) Provisional application No. 60/179,684, filed on Feb. 2, 2000.

(51) Int. Cl.$^7$ .................. C07D 213/36; C07D 305/14; A61K 31/337; A61K 31/4427; A61K 31/381

(52) U.S. Cl. .................. 546/281.7; 514/337; 514/444; 514/471; 514/473; 514/449; 549/60; 549/471; 549/510; 549/511

(58) Field of Search ............................ 549/510, 511, 549/60, 471; 514/449, 337, 444, 471, 473; 546/281.7

(56) References Cited

U.S. PATENT DOCUMENTS

| | | |
|---|---|---|
| 5,175,315 A | 12/1992 | Holton |
| 5,227,400 A | 7/1993 | Holton et al. |
| 5,243,045 A | 9/1993 | Holton et al. |
| 5,254,580 A | 10/1993 | Chen et al. |
| 5,283,253 A | 2/1994 | Holton et al. |
| 5,350,866 A | 9/1994 | Holton et al. |
| 5,407,674 A | 4/1995 | Gabetta et al. |
| 5,430,160 A | 7/1995 | Holton |
| 5,475,011 A | 12/1995 | Ojima et al. |
| 5,556,878 A | 9/1996 | Kelley et al. |
| 5,567,614 A | 10/1996 | Patel et al. |
| 5,614,645 A | 3/1997 | Kingston et al. |
| 5,698,712 A | 12/1997 | Bombardelli et al. |
| 5,714,513 A | 2/1998 | Holton et al. |
| 5,721,268 A | 2/1998 | Holton et al. |
| 5,780,653 A | 7/1998 | Tao et al. |
| 5,811,452 A | 9/1998 | Ojima et al. |
| 5,879,929 A | 3/1999 | Patel |
| 5,906,990 A | 5/1999 | Bouchard et al. |
| 5,912,264 A | 6/1999 | Wittman et al. |
| 5,939,561 A | 8/1999 | Bourzat et al. |
| 5,959,125 A | 9/1999 | Bouchard et al. |
| 5,965,739 A | 10/1999 | Kelly et al. |
| 6,100,411 A * | 8/2000 | Ojima .................. 549/510 |
| 6,214,863 B1 | 4/2001 | Bissery |

FOREIGN PATENT DOCUMENTS

| | | |
|---|---|---|
| EP | 0 558 959 B1 | 9/1993 |
| EP | 0 590 267 A2 A3 | 4/1994 |
| EP | 0 600 517 B1 | 6/1994 |
| EP | 0 604 910 B1 | 7/1994 |
| EP | 0 629 701 B1 | 12/1994 |
| EP | 0 639 577 A1 | 2/1995 |
| EP | 0 712 854 A1 | 5/1996 |
| JP | 10-045583 | 2/1998 |
| RU | 951134214 A1 | 3/1994 |
| WO | WO 93/23389 A1 | 11/1993 |
| WO | WO 96/38138 A1 | 12/1993 |
| WO | WO 94/13655 A1 | 6/1994 |
| WO | WO 94/20484 A1 | 9/1994 |
| WO | WO 96/13495 A1 | 5/1996 |
| WO | WO 97/09979 A1 | 3/1997 |
| WO | WO 97/32578 A1 | 9/1997 |
| WO | WO 97/42181 A1 | 11/1997 |
| WO | WO 98/02426 A1 | 1/1998 |
| WO | WO 99/09021 A1 | 2/1999 |
| WO | WO 00/53592 A1 | 9/2000 |
| WO | WO 01/57013 A1 | 8/2001 |
| WO | WO 01/57031 A1 | 8/2001 |

OTHER PUBLICATIONS

Gueritte–Voegelein et al. "Chemical Studies of 10–Deacetyl Baccatin III. Hemisynthesis of Taxol Derivatives" Tetrahedron Letters. vol. 42, No. 16 (1986) pp. 4451–4460.

Gueritte–Voegelein et al. "Relationships between the Structure of Taxol Analogues and Their Antimitotic Activity" Journal of Medicinal Ch–emistry, vol. 34, No. 3 (1991) pp. 992–998.

Kant et al. "A Chemoselective Approach to Functionalize the C–10 Position of 10–Deacetylbaccatin III. Synthesis and Biological Properties of Novel C–10 Taxol Analogues" Tetrahedron Letters, vol. 35, No. 30 (1994) pp. 5543–5546.

Ojima et al. "Enantiopure Fluorine–Containing Taxoids: Potent Anticancer Agents and Verstile Probes for Biomedical Problems" Journal of Fluorine Chemistry, vol. 97 (1999) pp. 3–10.

Ojima et al. "Synthesis and Structure–Activity Relationships of the Second–Generation Antitumor Taxoids: Exceptional Activity Against Drug–Resistant Cancer Cells" Journal of Medicinal Chemistry, vol. 36 (1996) pp. 3889–3896.

Ojima et al. "Synthesis and Biological Activity of Novel 3'–Trifluoromethyl Taxoids" Bioorganic & Medicinal Chemistry Letters, vol. 7, No. 2 (1997) pp. 133–138.

Ojima et al. "Synthesis of Novel 3'–Trifluoromethyl Taxoids Through Effective Kinetic Resolution of Racemic 4–CF$_3$–β–Lactams With Baccatins" Chirality, vol. 9 (1997) pp. 487–494.

Straubinger et al. "Pharmacology and Antitumor Effect of Novel Placlitaxel Formulatins" Chapter 8, Edited by G. Georg et al., Taxane Anticancer Agents, Basic Science and Current Status, ACS Symposium Series 583, 207th National Meeting of the American Chemistry Society, San Diego, CA (1994) pp. 111–123.

Georgia Search Report from AP 2001 004501 dtd Feb. 06, 2003.

\* cited by examiner

*Primary Examiner*—Ba K. Trinh
(74) *Attorney, Agent, or Firm*—Senniger, Powers, Leavitt & Roedel

(57) ABSTRACT

Taxanes having a carbonate substituent at C(10), a hydroxy substituent at C(7), and a range of C(2), C(9), C(14), and side chain substituents.

117 Claims, No Drawings

C10 CARBONATE SUBSTITUTED TAXANES

REFERENCE TO RELATED APPLICATION

This application claims priority from U.S. provisional application Serial No. 60/179,684, filed on Feb. 2, 2000.

BACKGROUND OF THE INVENTION

The present invention is directed to novel taxanes which have exceptional utility as antitumor agents.

The taxane family of terpenes, of which baccatin III and taxol are members, has been the subject of considerable interest in both the biological and chemical arts. Taxol itself is employed as a cancer chemotherapeutic agent and possesses a broad range of tumor-inhibiting activity. Taxol has a 2'R, 3'S configuration and the following structural formula:

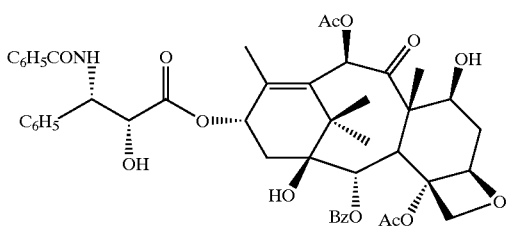

wherein Ac is acetyl.

Colin et al. reported in U.S. Pat. No. 4,814,470 that certain taxol analogs have an activity significantly greater than that of taxol. One of these analogs, commonly referred to as docetaxel, has the following structural formula:

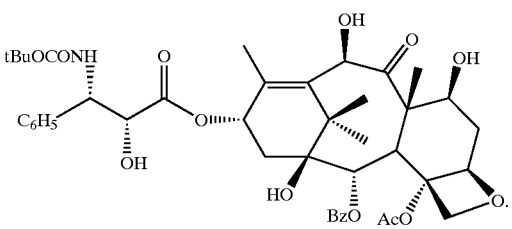

Although taxol and docetaxel are useful chemotherapeutic agents, there are limitations on their effectiveness, including limited efficacy against certain types of cancers and toxicity to subjects when administered at various doses. Accordingly, a need remains for additional chemotherapeutic agents with improved efficacy and less toxicity.

SUMMARY OF THE INVENTION

Among the objects of the present invention, therefore, is the provision of taxanes which compare favorably to taxol and docetaxel with respect to efficacy as anti-tumor agents and with respect to toxicity. In general, these taxanes possess a carbonate substituent at C(10), a hydroxy substituent at C(7), and a range of C(2), C(9), C(14), and C(13) side chain substituents.

Briefly, therefore, the present invention is directed to the taxane composition, per se, to pharmaceutical compositions comprising the taxane and a pharmaceutically acceptable carrier, and to methods of administration.

Other objects and features of this invention will be in part apparent and in part pointed out hereinafter.

DETAILED DESCRIPTION OF THE PREFERRED EMBODIMENTS

In one embodiment of the present invention, the taxanes of the present invention correspond to structure (1):

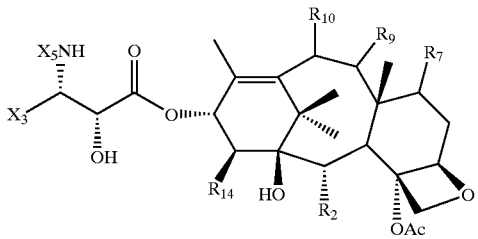

(1)

wherein
$R_2$ is acyloxy;
$R_7$ is hydroxy;
$R_9$ is keto, hydroxy, or acyloxy;
$R_{10}$ is carbonate;
$R_{14}$ is hydrido or hydroxy;
$X_3$ is substituted or unsubstituted alkyl, alkenyl, alkynyl, phenyl or heterocyclo, wherein alkyl comprises at least two carbon atoms;
$X_5$ is —$COX_{10}$, —$COOX_{10}$, or —$CONHX_{10}$;
$X_{10}$ is hydrocarbyl, substituted hydrocarbyl, or heterocyclo;
Ac is acetyl; and
$R_7$, $R_9$, and $R_{10}$ independently have the alpha or beta stereochemical configuration.

In one embodiment, $R_2$ is an ester ($R_{2a}C(O)O$—), a carbamate ($R_{2a}R_{2b}NC(O)O$—), a carbonate ($R_{2a}OC(O)O$—), or a thiocarbonate ($R_{2a}SC(O)O$—) wherein $R_{2a}$ and $R_{2b}$ are independently hydrogen, hydrocarbyl, substituted hydrocarbyl or heterocyclo. In a preferred embodiment, $R_2$ is an ester ($R_{2a}C(O)O$—), wherein $R_{2a}$ is aryl or heteroaromatic. In another preferred embodiment, $R_2$ is an ester ($R_{2a}C(O)O$—), wherein $R_{2a}$ is substituted or unsubstituted phenyl, furyl, thienyl, or pyridyl. In one particularly preferred embodiment, $R_2$ is benzoyloxy.

While $R_9$ is keto in one embodiment of the present invention, in other embodiments $R_9$ may have the alpha or beta stereochemical configuration, preferably the beta stereochemical configuration, and may be, for example, α- or β-hydroxy or α- or β-acyloxy. For example, when $R_9$ is acyloxy, it may be an ester ($R_{9a}C(O)O$—), a carbamate ($R_{9a}R_{9b}NC(O)O$—), a carbonate ($R_{9a}OC(O)O$—), or a thiocarbonate ($R_{9a}SC(O)O$—) wherein $R_{9a}$ and $R_{9b}$ are independently hydrogen, hydrocarbyl, substituted hydrocarbyl or heterocyclo. If $R_9$ is an ester ($R_{9a}C(O)O$—), $R_{9a}$ is substituted or unsubstituted alkyl, substituted or unsubstituted alkenyl, substituted or unsubstituted aryl or substituted or unsubstituted heteroaromatic. Still more preferably, $R_9$ is an ester ($R_{9a}C(O)O$), wherein $R_{9a}$ is substituted or unsubstituted phenyl, substituted or unsubstituted furyl, substituted or unsubstituted thienyl, or substituted or unsubstituted pyridyl. In one embodiment $R_9$ is ($R_{9a}C(O)O$—) wherein $R_{9a}$ is methyl, ethyl, propyl (straight, branched or cyclic), butyl (straight, branched or cyclic), pentyl, (straight, branched or cyclic), or hexyl (straight, branched or cyclic). In another embodiment $R_9$ is ($R_{9a}C(O)O$—) wherein $R_{9a}$ is substituted methyl, substituted ethyl, substituted propyl (straight, branched or cyclic), substituted butyl (straight, branched or cyclic), substituted pentyl, (straight, branched or cyclic), or substituted hexyl (straight, branched or cyclic) wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

In one embodiment, $R_{10}$ is $R_{10a}OCOO$— wherein $R_{10a}$ is (i) substituted or unsubstituted $C_1$ to $C_8$ alkyl (straight, branched or cyclic), such as methyl, ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heterocyclo such as furyl, thienyl, or pyridyl. The substituents may be hydrocarbyl or any of the heteroatom containing substituents identified elsewhere herein for substituted hydrocarbyl. In a preferred embodiment, $R_{10a}$ is methyl, ethyl, straight, branched or cyclic propyl, straight, branched or cyclic butyl, straight, branched or cyclic hexyl, straight or branched propenyl, isobutenyl, furyl or thienyl. In another embodiment, $R_{10a}$ is substituted ethyl, substituted propyl (straight, branched or cyclic), substituted propenyl (straight or branched), substituted isobutenyl, substituted furyl or substituted thienyl wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

Exemplary $X_3$ substituents include substituted or unsubstituted $C_2$ to $C_8$ alkyl, substituted or unsubstituted $C_2$ to $C_8$ alkenyl, substituted or unsubstituted $C_2$ to $C_8$ alkynyl, substituted or unsubstituted heteroaromatics containing 5 or 6 ring atoms, and substituted or unsubstituted phenyl. Exemplary preferred $X_3$ substituents include substituted or unsubstituted ethyl, propyl, butyl, cyclopropyl, cyclobutyl, cyclohexyl, isobutenyl, furyl, thienyl, and pyridyl.

Exemplary $X_5$ substituents include —$COX_{10}$, —$COOX_{10}$ or —$CONHX_{10}$ wherein $X_{10}$ is substituted or unsubstituted alkyl, alkenyl, phenyl or heteroaromatic. Exemplary preferred $X_5$ substituents include —$COX_{10}$, —$COOX_{10}$ or —$CONHX_{10}$ wherein $X_{10}$ is (i) substituted or unsubstituted $C_1$ to $C_8$ alkyl such as substituted or unsubstituted methyl, ethyl, propyl (straight, branched or cyclic), butyl (straight, branched or cyclic), pentyl (straight, branched or cyclic), or hexyl (straight, branched or cyclic); (ii) substituted or unsubstituted $C_2$ to $C_8$ alkenyl such as substituted or unsubstituted ethenyl, propenyl (straight, branched or cyclic), butenyl (straight, branched or cyclic), pentenyl (straight, branched or cyclic) or hexenyl (straight, branched or cyclic); (iii) substituted or unsubstituted $C_2$ to $C_8$ alkynyl such as substituted or unsubstituted ethynyl, propynyl (straight or branched), butynyl (straight or branched), pentynyl (straight or branched), or hexynyl (straight or branched); (iv) substituted or unsubstituted phenyl, or (v) substituted or unsubstituted heteroaromatic such as furyl, thienyl, or pyridyl, wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

In one embodiment, the taxanes of the present invention correspond to structure (2):

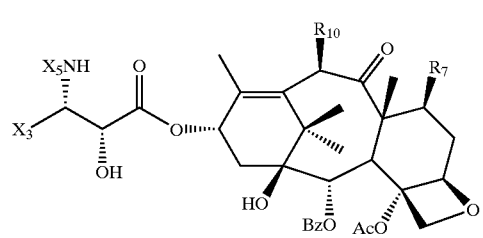

(2)

wherein
$R_7$ is hydroxy;
$R_{10}$ is carbonate;
$X_3$ is substituted or unsubstituted alkyl, alkenyl, alkynyl, or heterocyclo, wherein alkyl comprises at least two carbon atoms;
$X_5$ is —$COX_{10}$, —$COOX_{10}$, or —$CONHX_{10}$; and
$X_{10}$ is hydrocarbyl, substituted hydrocarbyl, or heterocyclo.

For example, in this preferred embodiment in which the taxane corresponds to structure (2), $R_{10}$ may be $R_{10a}OCOO$— wherein $R_{10a}$ is substituted or unsubstituted methyl, ethyl, propyl, butyl, pentyl or hexyl, more preferably substituted or unsubstituted methyl, ethyl or propyl, still more preferably substituted or unsubstituted methyl, ethyl, and still more preferably unsubstituted methyl or ethyl. While $R_{7a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{10a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{10a}$ and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure 2 in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{10a}$ is unsubstituted methyl, ethyl or propyl, more preferably methyl or ethyl.

Among the preferred embodiments are taxanes corresponding to structure 1 or 2 wherein $R_{10}$ is $R_{10a}OCOO$— wherein $R_{10a}$ is methyl. In this embodiment, $X_3$ is preferably cycloalkyl, isobutenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl, still more preferably t-butoxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_{10}$ is $R_{10a}$OCOO— wherein $R_{10a}$ is ethyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_{10}$ is $R_{10a}$OCOO— wherein $R_{10a}$ is propyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Taxanes having the general formula 1 may be obtained by treatment of a β-lactam with an alkoxide having the taxane tetracyclic nucleus and a C-13 metallic oxide substituent to form compounds having β-amido ester substituent at C(13), as described more fully in Holton U.S. Pat. No. 5,466,834, followed by removal of the hydroxy protecting groups. The β-lactam has the following structural formula (3):

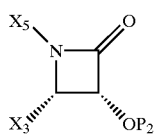

(3)

wherein $P_2$ is a hydroxy protecting group and $X_3$ and $X_5$ are as previously defined and the alkoxide has the structural formula (4):

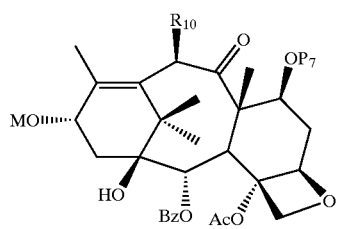

(4)

wherein M is a metal or ammonium, $P_7$ is a hydroxy protecting group and $R_{10}$ is as previously defined.

The alkoxide may be prepared from 10-deacetylbaccatin III by selective formation of a carbonate of the C-10 hydroxyl group and then protection of the C-7 hydroxyl group (as described more fully in Holton et al., PCT Patent Application WO 99/09021, followed by treatment with a metallic amide. Acylating agents which may be used for the selective acylation of the C(10) hydroxyl group of a taxane include dimethyidicarbonate, diethyidicarbonate, di-t-butyidicarbonate, dibenzyldicarbonate and the like. While the acylation of the C(10) hydroxy group of the taxane will proceed at an adequate rate for many acylating agents, it has been discovered that the reaction rate may be increased by including a Lewis acid in the reaction mixture. Preferred Lewis acids include zinc chloride, stannic chloride, cerium trichloride, cuprous chloride, lanthanum trichloride, dysprosium trichloride, and ytterbium trichloride. Zinc chloride or cerium trichloride is particularly preferred when the acylating agent is a dicarbonate.

Derivatives of 10-deacetylbaccatin III having alternative substituents at C(2), C(9) and C(14) and processes for their preparation are known in the art. Taxane derivatives having acyloxy substituents other than benzoyloxy at C(2) may be prepared, for example, as described in Holton et al., U.S. Pat. No. 5,728,725 or Kingston et al., U.S. Pat. No. 6,002,023. Taxanes having acyloxy or hydroxy substituents at C(9) in place of keto may be prepared, for example as described in Holton et al., U.S. Pat. No. 6,011,056 or Gunawardana et al., U.S. Pat. No. 5,352,806. Taxanes having a beta hydroxy substituent at C(14) may be prepared from naturally occurring 14-hydroxy-10-deacetylbaccatin III.

Processes for the preparation and resolution of the β-lactam starting material are generally well known. For example, the β-lactam may be prepared as described in Holton, U.S. Pat. No. 5,430,160 and the resulting enatiomeric mixtures of β-lactams may be resolved by a stereoselective hydrolysis using a lipase or enzyme as described, for example, in Patel, U.S. Pat. No. 5,879,929 Patel U.S. Pat. No. 5,567,614 or a liver homogenate as described, for example, in PCT Patent Application No. 00/41204. In a preferred embodiment in which the β-lactam is furyl substituted at the C(4) position, the β-lactam can be prepared as illustrated in the following reaction scheme:

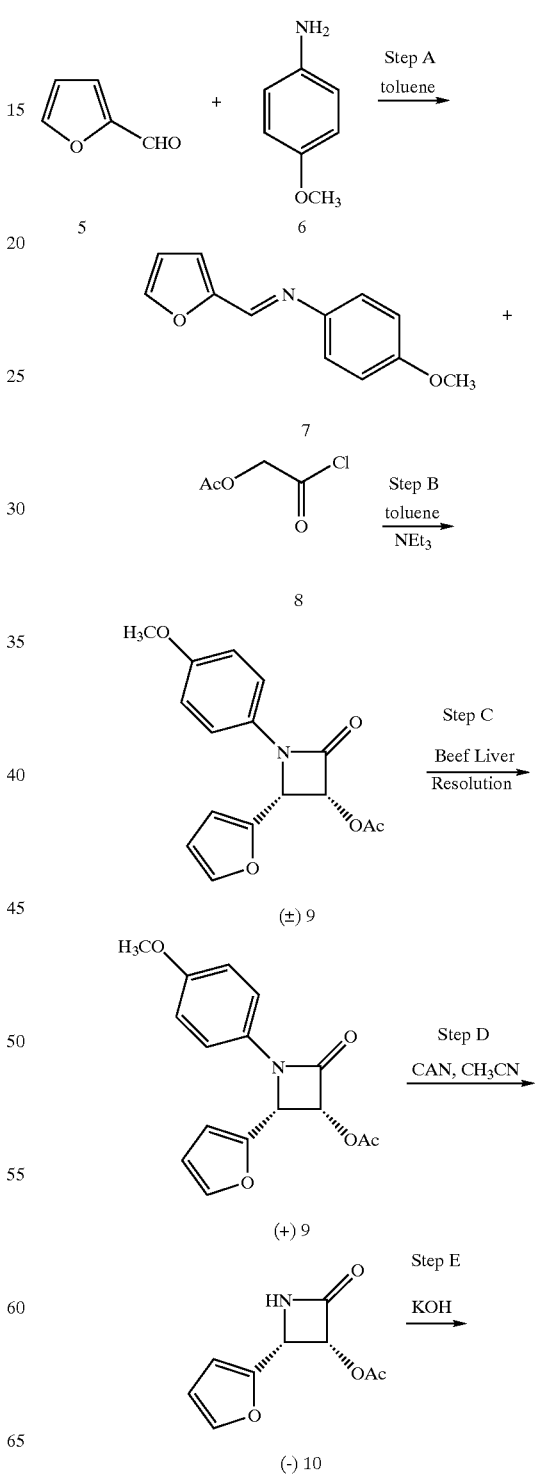

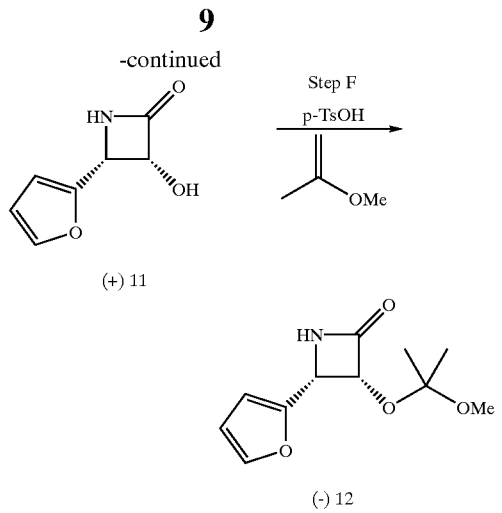

wherein Ac is acetyl, NEt₃ is triethylamine, CAN is ceric ammonium nitrate, and p-TsOH is p-toluenesulfonic acid. The beef liver resolution may be carried out, for example, by combining the enatiomeric β-lactam mixture with a beef liver suspension (prepared, for example, by adding 20 g of frozen beef liver to a blender and then adding a pH 8 buffer to make a total volume of 1 L).

Compounds of formula 1 of the instant invention are useful for inhibiting tumor growth in mammals including humans and are preferably administered in the form of a pharmaceutical composition comprising an effective antitumor amount of a compound of the instant invention in combination with at least one pharmaceutically or pharmacologically acceptable carrier. The carrier, also known in the art as an excipient, vehicle, auxiliary, adjuvant, or diluent, is any substance which is pharmaceutically inert, confers a suitable consistency or form to the composition, and does not diminish the therapeutic efficacy of the antitumor compounds. The carrier is "pharmaceutically or pharmacologically acceptable" if it does not produce an adverse, allergic or other untoward reaction when administered to a mammal or human, as appropriate.

The pharmaceutical compositions containing the antitumor compounds of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular antitumor compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, in: *Remington's Pharmaceutical Science* (A. Gennaro, ed.), Mack Publishing Co., Easton, Pa., (1985), pp. 1492–1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

The compositions of the invention for oral administration comprise an effective antitumor amount of a compound of the invention in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption.

The antitumor compounds of the present invention are also preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective antitumor amount of the antitumor compound in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2–30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamideamides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ monoricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4-C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2–30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3–30 carbon atoms (e.g., acetone, methyl ethyl ketone, methyl isobutyl ketone); aliphatic, cycloaliphatic or aromatic hydrocarbons having 4–30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1–30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.,)(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacoieia 24, The National Formulary 19*, (National Publishing, Philadelphia, Pa., 2000), A. J. Spiegel et al., and Use of Nonaqueous Solvents in Parenteral Products, *Journal of Pharmaceutical Sciences*, Vol. 52, No. 10, pp. 917–927 (1963).

Preferred solvents include those known to stabilize the antitumor compounds, such as oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor® EL solution or Cremophor® RH 40 solution). Commercially available triglycerides include Intralipid® emulsified soybean oil (Kabi-Pharmacia Inc., Stockholm, Sweden), Nutralipid ® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®. Ethanol is a preferred solvent for use in dissolving the antitumor compound to form solutions, emulsions, and the like.

Additional minor components can be included in the compositions of the invention for a variety of purposes well known in the pharmaceutical industry. These components will for the most part impart properties which enhance retention of the antitumor compound at the site of administration, protect the stability of the composition, control the pH, facilitate processing of the antitumor compound into pharmaceutical formulations, and the like. Preferably, each of these components is individually present in less than about 15 weight % of the total composition, more preferably less than about 5 weight %, and most preferably less than about 0.5 weight % of the total composition. Some components, such as fillers or diluents, can constitute up to 90 wt. % of the total composition, as is well known in the formulation art. Such additives include cryoprotective agents for preventing reprecipitation of the taxane, surface active, wetting or emulsifying agents (e.g., lecithin, polysorbate-80, Tween® 80, pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

In a preferred embodiment, a pharmaceutical composition of the invention comprises at least one nonaqueous, pharmaceutically acceptable solvent and an antitumor compound having a solubility in ethanol of at least about 100, 200, 300, 400, 500, 600, 700 or 800 mg/ml. While not being bound to a particular theory, it is believed that the ethanol solubility of the antitumor compound may be directly related to its efficacy. The antitumor compound can also be capable of being crystallized from a solution. In other words, a crystalline antitumor compound, such as compound 1393, can be dissolved in a solvent to form a solution and then recrystallized upon evaporation of the solvent without the formation of any amorphous antitumor compound. It is also preferred that the antitumor compound have an ID50 value (i.e, the drug concentration producing 50% inhibition of colony formation) of at least 4, 5, 6, 7, 8, 9, or 10 times less that of paclitaxel when measured according to the protocol set forth in the working examples.

Dosage form administration by these routes may be continuous or intermittent, depending, for example, upon the patient's physiological condition, whether the purpose of the administration is therapeutic or prophylactic, and other factors known to and assessable by a skilled practitioner.

Dosage and regimens for the administration of the pharmaceutical compositions of the invention can be readily determined by those with ordinary skill in treating cancer. It is understood that the dosage of the antitumor compounds will be dependent upon the age, sex, health, and weight of the recipient, kind of concurrent treatment, if any, frequency of treatment, and the nature of the effect desired. For any mode of administration, the actual amount of antitumor compound delivered, as well as the dosing schedule necessary to achieve the advantageous effects described herein, will also depend, in part, on such factors as the bioavailability of the antitumor compound, the disorder being treated, the desired therapeutic dose, and other factors that will be apparent to those of skill in the art. The dose administered to an animal, particularly a human, in the context of the present invention should be sufficient to effect the desired therapeutic response in the animal over a reasonable period of time. Preferably, an effective amount of the antitumor compound, whether administered orally or by another route, is any amount which would result in a desired therapeutic response when administered by that route. Preferably, the compositions for oral administration are prepared in such a way that a single dose in one or more oral preparations contains at least 20 mg of the antitumor compound per $m^2$ of patient body surface area, or at least 50, 100, 150, 200, 300, 400, or 500 mg of the antitumor compound per $m^2$ of patient body surface area, wherein the average body surface area for a human is 1.8 $m^2$. Preferably, a single dose of a composition for oral administration contains from about 20 to about 600 mg of the antitumor compound per $m^2$ of patient body surface area, more preferably from about 25 to about 400 mg/$m^2$, even more preferably, from about 40 to about 300 mg/$m^2$, and even more preferably from about 50 to about 200 mg/$l^2$. Preferably, the compositions for parenteral administration are prepared in such a way that a single dose contains at least 20 mg of the antitumor compound per $m^2$ of patient body surface area, or at least 40, 50, 100, 150, 200, 300, 400, or 500 mg of the antitumor compound per $m^2$ of patient body surface area. Preferably, a single dose in one or more parenteral preparations contains from about 20 to about 500 mg of the antitumor compound per $m^2$ of patient body surface area, more preferably from about 40 to about 400 Mg/$m^2$, and even more preferably, from about 60 to about 350 mg/$m^2$. However, the dosage may vary depending on the dosing schedule which can be adjusted as necessary to achieve the desired therapeutic effect. It should be noted that the ranges of effective doses provided herein are not intended to limit the invention and represent preferred dose ranges. The most preferred dosage will be tailored to the individual subject, as is understood and determinable by one of ordinary skill in the art without undue experimentation.

The concentration of the antitumor compound in a liquid pharmaceutical composition is preferably between about 0.01 mg and about 10 mg per ml of the composition, more preferably between about 0.1 mg and about 7 mg per ml, even more preferably between about 0.5 mg and about 5 mg per ml, and most preferably between about 1.5 mg and about 4 mg per ml. Relatively low concentrations are generally preferred because the antitumor compound is most soluble in the solution at low concentrations. The concentration of the antitumor compound in a solid pharmaceutical composition for oral administration is preferably between about 5 weight % and about 50 weight %, based on the total weight of the composition, more preferably between about 8 weight % and about 40 weight %, and most preferably between about 10 weight % and about 30 weight %.

In one embodiment, solutions for oral administration are prepared by dissolving an antitumor compound in any pharmaceutically acceptable solvent capable of dissolving the compound (e.g., ethanol or methylene chloride) to form a solution. An appropriate volume of a carrier which is a solution, such as Cremophor® EL solution, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving an antitumor compound in any pharmaceutically acceptable solvent capable of dissolving the compound (e.g.,ethanol or methylene chloride) to form a solution. The solvent can optionally be capable of evaporating when the solution is dried under vacuum. An additional carrier can be added to the solution prior to drying, such as Cremophor® EL solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving an antitumor compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsion, is added to the solution while stirring to form a pharmaceutically acceptable emulsion for parenteral administration to a patient. If desired, such emulsions can be formulated to contain a minimal amount of, or to be free of, ethanol or Cremophor® solution, which are known in the art to cause adverse physiological effects when administered at certain concentrations in parenteral formulations.

Solutions for parenteral administration can be prepared by dissolving an antitumor compound in any pharmaceutically acceptable solvent capable of dissolving the compound (e.g., ethanol or methylene chloride) to form a solution.

An appropriate volume of a carrier which is a solution, such as Cremophor® solution, is added to the solution while stirring to form a pharmaceutically acceptable solution for parenteral administration to a patient. If desired, such solutions can be formulated to contain a minimal amount of, or to be free of, ethanol or Cremophor® solution, which are known in the art to cause adverse physiological effects when administered at certain concentrations in parenteral formulations.

If desired, the emulsions or solutions described above for oral or parenteral administration can be packaged in IV bags, vials or other conventional containers in concentrated form and diluted with any pharmaceutically acceptable liquid, such as saline, to form an acceptable taxane concentration prior to use as is known in the art.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O) O— wherein R is as defined in connection with the term "acyl."

Unless otherwise indicated, the alkoxycarbonyloxy moieties described herein comprise lower hydrocarbon or substituted hydrocarbon or substituted hydrocarbon moieties.

Unless otherwise indicated, the carbamoyloxy moieties described herein are derivatives of carbamic acid in which one or both of the amine hydrogens is optionally replaced by a hydrocarbyl, substituted hydrocarbyl or heterocyclo moiety.

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, benzyloxymethyl, (.beta.-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

As used herein, "Ac" means acetyl; "Bz" means benzoyl; "Et" means ethyl; "Me" means methyl; "Ph" means phenyl; "iPr" means isopropyl; "tBu" and "t-Bu" means tert-butyl; "R" means lower alkyl unless otherwise defined; "py" means pyridine or pyridyl; "TES" means triethylsilyl; "TMS" means trimethylsilyl; "LAH" means lithium aluminum hydride; "10-DAB" means 10-desacetylbaccatin III"; "amine protecting group" includes, but is not limited to, carbamates, for example, 2,2,2-trichloroethylcarbamate or tertbutylcarbamate; "protected hydroxy" means —OP wherein P is a hydroxy protecting group; "tBuOCO" and "BOC" mean tert-butoxycarbonyl; "tAmOCO" means tert-amyloxycarbonyl; "PhCO" means phenylcarbonyl; "2-FuCO" means 2-furylcarbonyl; "2-ThCO" means 2-thienylcarbonyl; "2-PyCO" means 2-pyridylcarbonyl; "3-PyCO" means 3-pyridylcarbonyl; "4-PyCO" means 4-pyridylcarbonyl; "C$_4$H$_7$CO" means butenylcarbonyl; "tC$_3$H$_5$CO" means trans-propenylcarbonyl; "EtOCO" means ethoxycarbonyl; "ibueCO" means isobutenylcarbonyl; "iBuCO" means isobutylcarbonyl; "iBuOCO" means isobutoxycarbonyl; "iPrOCO" means isopropyloxycarbonyl; "nPrOCO" means n-propyloxycarbonyl; "nPrCO" means n-propylcarbonyl; "ibue" means isobutenyl; "THF" means tetrahydrofuran; "DMAP" means 4-dimethylamino pyridine; "LHMDS" means Lithium HexamethylDisilazanide.

The following examples illustrate the invention.

EXAMPLE 1

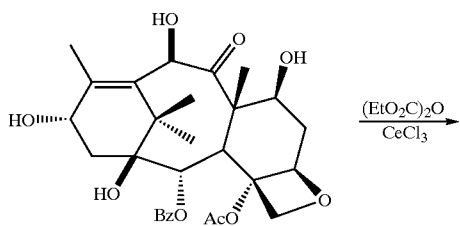

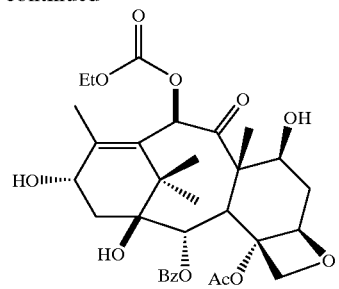

10-Ethoxycarbonyl-10-deacetyl baccatin III. To a mixture of 0.941 g (1.73 mmol) of 10-deacetyl baccatin III and 0.043 g (0.17 mmol) of CeCl$_3$ in 40 mL of THF at 25° C. was added 0.64 mL (4.32 mmol) of diethyl pyrocarbonate. After 3 h the reaction mixture was diluted with 200 mL of EtOAc, then washed three times with 50 mL of saturated aqueous NaHCO$_3$ solution and brine. The organic extract was dried over Na$_2$SO$_4$ and concentrated in vacuo. The crude solid was purified by flash column chromatography on silica gel using 40% EtOAc/hexane as eluent to give 0.960 g (90%) of 10-ethoxycarbonyl-10-deacetyl baccatin III as a solid.

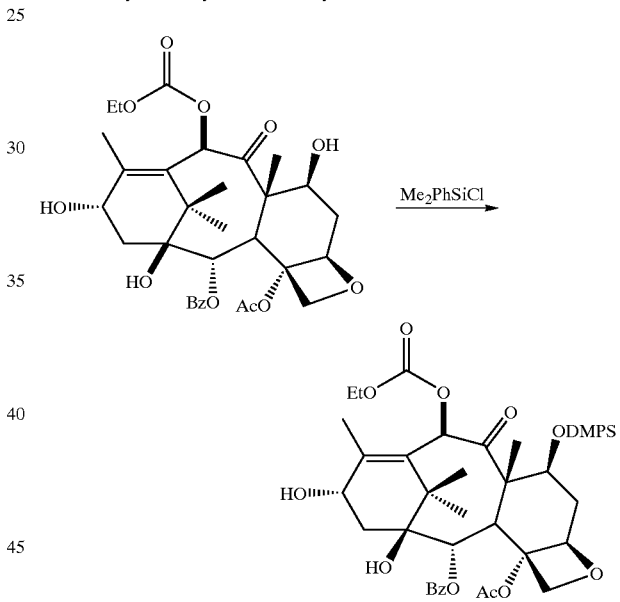

7-Dimethylphenylsilyl-10-ethoxycarbonyl-10-deacetyl baccatin III. To a solution of 1.02 g (1.65 mmol) of 10-ethoxycarbonyl-10-deacetyl baccatin III in 30 mL of THF at −10° C. under a nitrogen atmosphere was added dropwise 0.668 mL (4.00 mmol) of chlorodimethylphenylsilane and 2.48 mL (30.64 mmol) of pyridine. After 90 min the mixture was diluted with 200 mL of a 1:1 mixture of ethyl acetate and hexane. The mixture was washed with 30 mL of saturated aqueous sodium bicarbonate solution and the organic layer separated. The aqueous layer was extracted with 50 mL of a 1:1 mixture of ethyl acetate and hexane, and the combined organic extracts were washed with brine, dried over Na$_2$SO$_4$, and concentrated in vacuo. The crude solid was purified by flash column chromatography on silica gel using 30% EtOAc/hexane as eluent to give 1.16 g (94%) of 7-dimethylphenylsilyl-10-ethoxycarbonyl-10-deacetyl baccatin III as a solid. $^1$HNMR(400 MHz, CDCl$_3$): d 8.09 (dm, J=7.64 Hz, 2H, benzoate, o), 7.59 (tt, J=7.54, 1.43 Hz, 1H, benzoate, p), 7.57 (m, 2H, phenyl, o), 7.46 (t, J=7.54 Hz, 2H, benzoate, m), 7.37–7.33 (m, 3H, phenyl, m,p), 6.21 (s, 1H, H10), 5.63 (d, J=7.05 Hz, 1H, H2), 4.87–4.80 (m, 2H, H5 and H13), 4.44 (dd, J=6.84, 10.37 Hz, 1H, H7), 4.27 (d, J=8.27 Hz, 1H, H20a), 4.16 (qm, J=7.00 Hz, 2H, CH₃—CH₂—), 4.13 (d, J=8.27 Hz, 1H, H20b), 3.83 (d, J=7.05 Hz, 1H, H3), 2.34 (ddd, J=6.84, 9.63, 14.66 Hz, 1H, H6a), 2.26 (d, J=7.65 Hz, 2H, H14a,b), 2.25 (s, 3H, Ac4), 2.03 (s, 3H, Me18), 1.98 (d, J=5.29, 1H, C13OH), 1.77 (ddd, J=2.12, 10.37, 14.66 Hz, 1H, H6b), 1.73 (s, 1H, Me19), 1.59 (s, 1H, C1OH), 1.32 (t, J=7.00 Hz, 3H, CH₃—CH₂—), 1.19 (s, 3H, Me17), 1.07 (s, 3H, Me16), 0.45 (s, 3H, PhMe₂Si—), 0.35 (s, 3H, PhMe₂Si—).

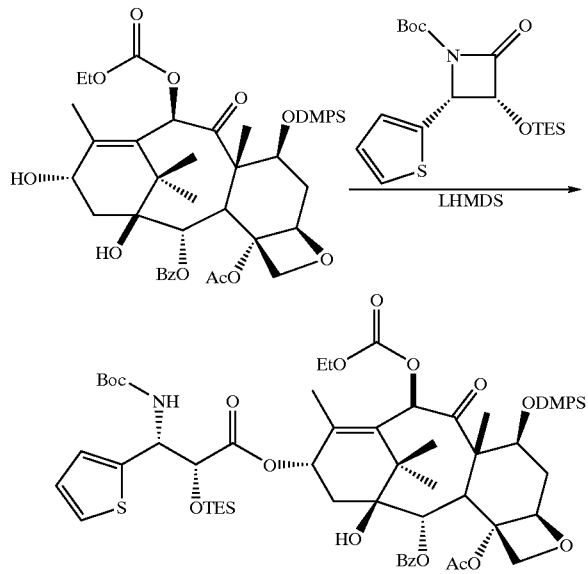

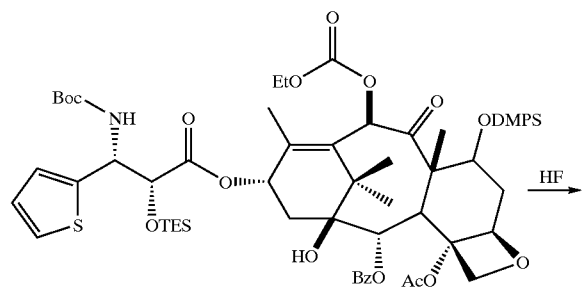

7-Dimethylphenylsilyl-2'-O-triethylsilyi-3'-desphenyl-3'-(2-thienyl)-10-ethoxycarbonyl-10-deacetyl taxotere. To a solution of 0.409 g (0.544 mmol) of 3,7-dimethylphenylsilyl-10-ethoxycarbonyl-10-deacetyl baccatin III in 5.5 mL of THF at −45° C. under a nitrogen atmosphere was added 0.681 mL (0.681 mmol) of a 1M solution of LHMDS in THF. After 1 h, a solution of 0.317 g (0.818 mmol) of cis-N-benzoyl-3-triethylsilyloxy4-(2-thienyl) azetidin-2-one in 3 mL of THF was added slowly. The mixture was warmed to 0° C. and after 3 h 10 mL of saturated aqueous sodium bicarbonate solution was added and the mixture was extracted three times with 50 mL of ethyl acetate. The combined organic extracts were washed with brine, dried over Na₂SO₄, and concentrated in vacuo. The crude product was purified by flash column chromatography on silica gel using 40% EtOAc/hexane as eluent to give 0.574 g (93%) of 7-dimethylphenylsilyl-2'-O-triethylsilyl-3'-desphenyl-3'-(2-thienyl)-10-ethoxycarbonyl-10-deacetyl taxotere as a solid.

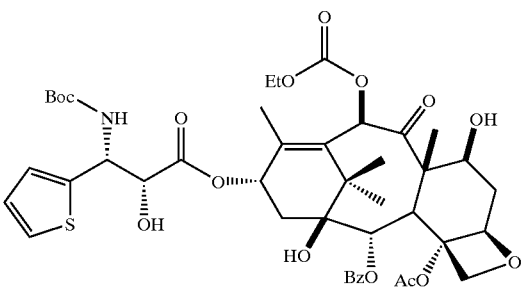

3'-Desphenyl-3'-(2-thienyl)-10-ethoxycarbonyl-10-deacetyl taxotere. To a solution of 0.527 g (0.464 mmol) of 7-dimethylphenylsilyl-2'-O-triethylsilyl-3'-desphenyl-3'-(2-thienyl)-10-ethoxycarbonyl-10-deacetyl taxotere in 2 mL of CH₃CN and 2 mL of pyridine at 0° C. was added 0.5 mL of a solution of 30% HF in H₂O. After 3 h 20 mL of a saturated aqueous sodium bicarbonate solution was added and the mixture was extracted three times with 50 mL of ethyl acetate. The combined organic extracts were washed with brine, dried over Na₂SO₄, and concentrated in vacuo. The crude product was purified by flash column chromatography on silica gel using 70% EtOAc/hexane as eluent to give 0.411 g (100%) of 3'-desphenyl-3'-(2-thienyl)-10-ethoxycarbonyl-10-deacetyl taxotere as a solid. m.p. 160–161° C.; $[\alpha]_D^{25}$=−59.1 (c 1.0 in CH₂Cl₂); Anal. Calcd. for $C_{44}H_{55}NO_{16}S$: C, 59.65; H, 6.26; Found: C, 59.39; H, 6.34.

3'-Desphenyl-3'-(2-thienyl)-10-ethoxycarbonyl-10-deacetyl Taxotere ¹H NMR Data (500 MHz, CDCl₃)

| Proton | d (ppm) | Pattern | J (Hz) |
|---|---|---|---|
| 1OH | 1.68 | s | |
| 2 | 5.68 | d | H3(7.0) |
| 3 | 3.80 | d | H3(7.0) |
| 4Ac | 2.38 | s | |
| 5 | 4.95 | dd | H6b(2.0), H6b(9.8) |
| 6a | 2.56 | ddd | H7(6.6), H5(9.8), H6b(14.65) |
| 6b | 1.89 | ddd | H5(2.0), H7(10.9), H6a(14.65) |
| 7 | 4.40 | ddd | C7OH(4.2), H6a(6.6), H6b(10.9) |
| 7OH | 2.50 | d | H7(4.2) |
| 10 | 6.12 | s | |
| 13 | 6.25 | t | H14a(9.1),H14b(9.1) |
| 14a | 2.35 | dd | H13(9.1), H14b(14.2) |
| 14b | 2.34 | dd | H13(9.1), H14a(14.2) |
| 16Me | 1.17 | s | |
| 17Me | 1.26 | s | |
| 18Me | 1.90 | s | |
| 19Me | 1.70 | s | |
| 20a | 4.31 | d | H20b(8.6) |
| 20b | 4.19 | d | H20a(8.6) |
| 2' | 4.64 | dd | C2'OH(5.5), H3'(2.0) |
| 2'OH | 3.38 | d | H3(5.5) |
| 3' | 5.51 | br d | NH(9.5) |
| NH | 5.28 | d | H3'(9.5) |
| 3'(2-thienyl), H3" | 7.29 | dd | 3'(2-thienyl), H5"(1.1), 3'(2-thienyl), H3"(5.1) |

-continued

| Proton | d (ppm) | Pattern | J (Hz) |
|---|---|---|---|
| 3'(2-thienyl), H4" | 7.02 | dd | 3'(2-thienyl), H5"(3.6), 3'(2-thienyl), H3"(5.1) |
| 3'(2-thienyl), H5" | 7.09 | d | 3'(2-thienyl), H4"(3.6) |
| Boc | 1.34 | s | |
| benzoate, m | 7.51 | t | benzoate, o(7.8), benzoate, p(7.8) |
| benzoate, o | 8.12 | d | benzoate, m(7.8) |
| benzoate, p | 7.61 | t | benzoate, m(7.8) |
| $CH_3$—$CH_2$—OCO | 1.37 | t | $CH_3$—$CH_2$—OCO(7.1) |
| $CH_3$—$CH_2$—OCO | 4.28 | m | |

EXAMPLE 2

The procedures described in Example 1 were repeated, but other suitably protected β-lactams were substituted for the β-lactam of Example 1 to prepare the series of compounds having structural formula (13) and the combinations of substituents identified in the following table.

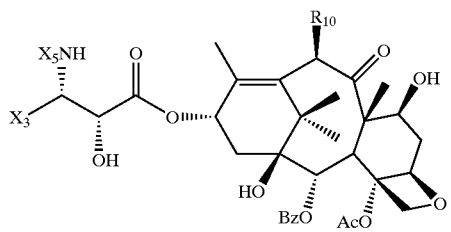

(13)

| Compound | $X_5$ | $X_3$ | $R_{10}$ |
|---|---|---|---|
| 1755 | tBuOCO— | 2-thienyl | EtOCOO— |
| 1767 | tBuOCO— | isopropyl | EtOCOO— |
| 1781 | tBuOCO— | isobutenyl | EtOCOO— |
| 1799 | tBuOCO— | 2-pyridyl | EtOCOO— |
| 1808 | tBuOCO— | 3-pyridyl | EtOCOO— |
| 1811 | tBuOCO— | 4-pyridyl | EtOCOO— |
| 1822 | tBuOCO— | 2-furyl | EtOCOO— |
| 1838 | tBuOCO— | 3-furyl | EtOCOO— |
| 1841 | tBuOCO— | 3-thienyl | EtOCOO— |
| 1855 | tBuOCO— | cyclobutyl | EtOCOO— |
| 1999 | tBuOCO— | isobutenyl | MeOCOO— |
| 2002 | tBuOCO— | 2-pyridyl | MeOCOO— |
| 2011 | tBuOCO— | 3-pyridyl | MeOCOO— |
| 2020 | tBuOCO— | 4-pyridyl | MeOCOO— |
| 2032 | tBuOCO— | 3-furyl | MeOCOO— |
| 2044 | tBuOCO— | 2-thienyl | MeOCOO— |
| 2050 | tBuOCO— | 3-thienyl | MeOCOO— |
| 2062 | tBuOCO— | isopropyl | MeOCOO— |
| 2077 | tBuOCO— | cyclobutyl | MeOCOO— |
| 2666 | tBuOCO— | 2-furyl | MeOCOO— |
| 2972 | PhCO— | 2-thienyl | EtOCOO— |
| 2988 | EtOCO— | 2-thienyl | EtOCOO— |
| 2999 | iPrOCO— | 2-thienyl | EtOCOO— |
| 3003 | iBuOCO— | 2-thienyl | EtOCOO— |
| 3011 | 2-FuCO— | 2-thienyl | EtOCOO— |
| 3020 | 2-ThCO— | 2-thienyl | EtOCOO— |
| 3033 | $C_4H_7$CO— | 2-thienyl | EtOCOO— |
| 3155 | nPrCO— | 2-thienyl | EtOCOO— |
| 3181 | iBuOCO— | 2-furyl | EtOCOO— |
| 3243 | $tC_3H_5$CO— | 2-thienyl | EtOCOO— |
| 3300 | 3-PyCO— | 2-thienyl | EtOCOO— |
| 3393 | 4-PyCO— | 2-thienyl | EtOCOO— |
| 3433 | 2-PyCO— | 2-thienyl | EtOCOO— |
| 3911 | 2-FuCO— | 2-furyl | EtOCOO— |
| 3929 | nPrCO— | 2-furyl | EtOCOO— |
| 3963 | iPrOCO— | 2-furyl | EtOCOO— |
| 4000 | $tC_3H_5$CO— | 2-furyl | EtOCOO— |

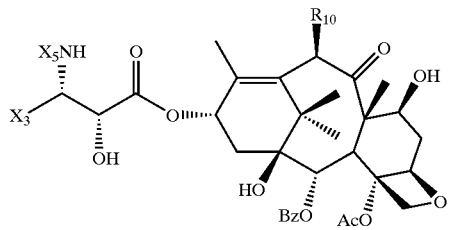

(13)

| Compound | $X_5$ | $X_3$ | $R_{10}$ |
|---|---|---|---|
| 4020 | EtOCO— | 2-furyl | EtOCOO— |
| 4074 | $C_4H_7$CO— | 2-furyl | EtOCOO— |
| 4088 | 2-ThCO— | 2-furyl | EtOCOO— |
| 4090 | PhCO— | 2-furyl | EtOCOO— |
| 4374 | ibueCO— | 2-thienyl | EtOCOO— |
| 4636 | iBuOCO— | 3-furyl | EtOCOO— |
| 6466 | iPrCO— | 2-furyl | EtOCOO— |
| 4959 | $tC_3H_5$CO— | 3-furyl | EtOCOO— |
| 4924 | iBuOCO— | 3-thienyl | EtOCOO— |
| 4844 | iBuOCO— | cpro | EtOCOO— |
| 5171 | tBuOCO— | cpro | EtOCOO— |
| 5155 | iBuOCO— | isobutenyl | EtOCOO— |
| 1788 | tBuOCO— | isobutenyl | EtOCOO— |
| 1767 | tBuOCO— | isopropyl | EtOCOO— |
| 1771 | tBuOCO— | phenyl | EtOCOO— |
| 1866 | tBuOCO— | p-nitrophenyl | EtOCOO— |
| 2060 | tBuOCO— | isopropyl | MeOCOO— |
| 2092 | tBuOCO— | phenyl | MeOCOO— |
| 2088 | tBuOCO— | p-nitrophenyl | MeOCOO— |

EXAMPLE 3

Following the processes described in Example 1 and elsewhere herein, the following specific taxanes having structural formula 14 may be prepared, wherein $R_{10}$ is as previously defined including wherein $R_{10}$ is $R_{10a}$OCOO— and $R_{10a}$ is (i) substituted or unsubstituted $C_1$ to $C_8$ alkyl such as methyl, ethyl, or straight, branched or cyclic propyl, butyl, pentyl, or hexyl; (ii) substituted or unsubstituted $C_3$ to $C_8$ alkenyl such as propenyl or straight, branched or cyclic butenyl, pentenyl or hexenyl; (iii) substituted or unsubstituted $C_3$ to $C_8$ alkynyl such as propynyl or straight or branched butynyl, pentynyl, or hexynyl; (iv) substituted or unsubstituted phenyl, or (v) substituted or unsubstituted heteroaromatic such as pyridyl. The substituents may be those identified elsewhere herein for substituted hydrocarbyl. For example, $R_{10}$ may be $R_{10a}$OCOO— wherein $R_{10a}$ is methyl, ethyl, or straight, branched or cyclic propyl.

(14)

| $X_5$ | $X_3$ | $R_{10}$ |
|---|---|---|
| tBuOCO | 2-furyl | $R_a$OCOO— |
| tBuOCO | 3-furyl | $R_a$OCOO— |

(14)

| X₅ | X₃ | R₁₀ |
|---|---|---|
| tBuOCO | 2-thienyl | RₐOCOO— |
| tBuOCO | 3-thienyl | RₐOCOO— |
| tBuOCO | 2-pyridyl | RₐOCOO— |
| tBuOCO | 3-pyridyl | RₐOCOO— |
| tBuOCO | 4-pyridyl | RₐOCOO— |
| tBuOCO | isobutenyl | RₐOCOO— |
| tBuOCO | isopropyl | RₐOCOO— |
| tBuOCO | cyclopropyl | RₐOCOO— |
| tBuOCO | cyclobutyl | RₐOCOO— |
| tBuOCO | cyclopentyl | RₐOCOO— |
| tBuOCO | phenyl | RₐOCOO— |
| benzoyl | 2-furyl | RₐOCOO— |
| benzoyl | 3-furyl | RₐOCOO— |
| benzoyl | 2-thienyl | RₐOCOO— |
| benzoyl | 3-thienyl | RₐOCOO— |
| benzoyl | 2-pyridyl | RₐOCOO— |
| benzoyl | 3-pyridyl | RₐOCOO— |
| benzoyl | 4-pyridyl | RₐOCOO— |
| benzoyl | isobutenyl | RₐOCOO— |
| benzoyl | isopropyl | RₐOCOO— |
| benzoyl | cyclopropyl | RₐOCOO— |
| benzoyl | cyclobutyl | RₐOCOO— |
| benzoyl | cyclopentyl | RₐOCOO— |
| benzoyl | phenyl | RₐOCOO— |
| 2-FuCO— | 2-furyl | RₐOCOO— |
| 2-FuCO— | 3-furyl | RₐOCOO— |
| 2-FuCO— | 2-thienyl | RₐOCOO— |
| 2-FuCO— | 3-thienyl | RₐOCOO— |
| 2-FuCO— | 2-pyridyl | RₐOCOO— |
| 2-FuCO— | 3-pyridyl | RₐOCOO— |
| 2-FuCO— | 4-pyridyl | RₐOCOO— |
| 2-FuCO— | isobutenyl | RₐOCOO— |
| 2-FuCO— | isopropyl | RₐOCOO— |
| 2-FuCO— | cyclopropyl | RₐOCOO— |
| 2-FuCO— | cyclobutyl | RₐOCOO— |
| 2-FuCO— | cyclopentyl | RₐOCOO— |
| 2-FuCO— | phenyl | RₐOCOO— |
| 2-ThCO— | 2-furyl | RₐOCOO— |
| 2-ThCO— | 3-furyl | RₐOCOO— |
| 2-ThCO— | 2-thienyl | RₐOCOO— |
| 2-ThCO— | 3-thienyl | RₐOCOO— |
| 2-ThCO— | 2-pyridyl | RₐOCOO— |
| 2-ThCO— | 3-pyridyl | RₐOCOO— |
| 2-ThCO— | 4-pyridyl | RₐOCOO— |
| 2-ThCO— | isobutenyl | RₐOCOO— |
| 2-ThCO— | isopropyl | RₐOCOO— |
| 2-ThCO— | cyclopropyl | RₐOCOO— |
| 2-ThCO— | cyclobutyl | RₐOCOO— |
| 2-ThCO— | cyclopentyl | RₐOCOO— |
| 2-ThCO— | phenyl | RₐOCOO— |
| 2-PyCO— | 2-furyl | RₐOCOO— |
| 2-PyCO— | 3-furyl | RₐOCOO— |
| 2-PyCO— | 2-thienyl | RₐOCOO— |
| 2-PyCO— | 3-thienyl | RₐOCOO— |
| 2-PyCO— | 2-pyridyl | RₐOCOO— |
| 2-PyCO— | 3-pyridyl | RₐOCOO— |
| 2-PyCO— | 4-pyridyl | RₐOCOO— |
| 2-PyCO— | isobutenyl | RₐOCOO— |
| 2-PyCO— | isopropyl | RₐOCOO— |
| 2-PyCO— | cyclopropyl | RₐOCOO— |
| 2-PyCO— | cyclobutyl | RₐOCOO— |
| 2-PyCO— | cyclopentyl | RₐOCOO— |
| 2-PyCO— | phenyl | RₐOCOO— |
| 3PyCO— | 2-furyl | RₐOCOO— |
| 3-PyCO— | 3-furyl | RₐOCOO— |
| 3-PyCO— | 2-thienyl | RₐOCOO— |
| 3-PyCO— | 3-thienyl | RₐOCOO— |
| 3-PyCO— | 2-pyridyl | RₐOCOO— |
| 3-PyCO— | 3-pyridyl | RₐOCOO— |
| 3-PyCO— | 4-pyridyl | RₐOCOO— |
| 3-PyCO— | isobutenyl | RₐOCOO— |
| 3-PyCO— | isopropyl | RₐOCOO— |
| 3-PyCO— | cyclopropyl | RₐOCOO— |
| 3-PyCO— | cyclobutyl | RₐOCOO— |
| 3-PyCO— | cyclopentyl | RₐOCOO— |
| 3-PyCO— | phenyl | RₐOCOO— |
| 4-PyCO— | 2-furyl | RₐOCOO— |
| 4-PyCO— | 3-furyl | RₐOCOO— |
| 4-PyCO— | 2-thienyl | RₐOCOO— |
| 4-PyCO— | 3-thienyl | RₐOCOO— |
| 4-PyCO— | 2-pyridyl | RₐOCOO— |
| 4-PyCO— | 3-pyridyl | RₐOCOO— |
| 4-PyCO— | 4-pyridyl | RₐOCOO— |
| 4-PyCO— | isobutenyl | RₐOCOO— |
| 4-PyCO— | isopropyl | RₐOCOO— |
| 4-PyCO— | cyclopropyl | RₐOCOO— |
| 4-PyCO— | cyclobutyl | RₐOCOO— |
| 4-PyCO— | cyclopentyl | RₐOCOO— |
| 4-PyCO— | phenyl | RₐOCOO— |
| C₄H₇CO— | 2-furyl | RₐOCOO— |
| C₄H₇CO— | 3-furyl | RₐOCOO— |
| C₄H₇CO— | 2-thienyl | RₐOCOO— |
| C₄H₇CO— | 3-thienyl | RₐOCOO— |
| C₄H₇CO— | 2-pyridyl | RₐOCOO— |
| C₄H₇CO— | 3-pyridyl | RₐOCOO— |
| C₄H₇CO— | 4-pyridyl | RₐOCOO— |
| C₄H₇CO— | isobutenyl | RₐOCOO— |
| C₄H₇CO— | isopropyl | RₐOCOO— |
| C₄H₇CO— | cyclopropyl | RₐOCOO— |
| C₄H₇CO— | cyclobutyl | RₐOCOO— |
| C₄H₇CO— | cyclopentyl | RₐOCOO— |
| C₄H₇CO— | phenyl | RₐOCOO— |
| EtOCO— | 2-furyl | RₐOCOO— |
| EtOCO— | 3-furyl | RₐOCOO— |
| EtOCO— | 2-thienyl | RₐOCOO— |
| EtOCO— | 3-thienyl | RₐOCOO— |
| EtOCO— | 2-pyridyl | RₐOCOO— |
| EtOCO— | 3-pyridyl | RₐOCOO— |
| EtOCO— | 4-pyridyl | RₐOCOO— |
| EtOCO— | isobutenyl | RₐOCOO— |
| EtOCO— | isopropyl | RₐOCOO— |
| EtOCO— | cyclopropyl | RₐOCOO— |
| EtOCO— | cyclobutyl | RₐOCOO— |
| EtOCO— | cyclopentyl | RₐOCOO— |
| EtOCO— | phenyl | RₐOCOO— |
| ibueCO— | 2-furyl | RₐOCOO— |
| ibueCO— | 3-furyl | RₐOCOO— |
| ibueCO— | 2-thienyl | RₐOCOO— |
| ibueCO— | 3-thienyl | RₐOCOO— |
| ibueCO— | 2-pyridyl | RₐOCOO— |
| ibueCO— | 3-pyridyl | RₐOCOO— |
| ibueCO— | 4-pyridyl | RₐOCOO— |
| ibueCO— | isobutenyl | RₐOCOO— |
| ibueCO— | isopropyl | RₐOCOO— |
| ibueCO— | cyclopropyl | RₐOCOO— |
| ibueCO— | cyclobutyl | RₐOCOO— |
| ibueCO— | cyclopentyl | RₐOCOO— |
| ibueCO— | phenyl | RₐOCOO— |

(14)

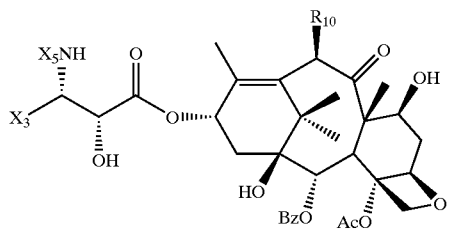

| X₅ | X₃ | R₁₀ |
|---|---|---|
| iBuCO— | 2-furyl | RₐOCOO— |
| iBuCO— | 3-furyl | RₐOCOO— |
| iBuCO— | 2-thienyl | RₐOCOO— |
| iBuCO— | 3-thienyl | RₐOCOO— |
| iBuCO— | 2-pyridyl | RₐOCOO— |
| iBuCO— | 3-pyridyl | RₐOCOO— |
| iBuCO— | 4-pyridyl | RₐOCOO— |
| iBuCO— | isobutenyl | RₐOCOO— |
| iBuCO— | isopropyl | RₐOCOO— |
| iBuCO— | cyclopropyl | RₐOCOO— |
| iBuCO— | cyclobutyl | RₐOCOO— |
| iBuCO— | cyclopentyl | RₐOCOO— |
| iBuCO— | phenyl | RₐOCOO— |
| iBuOCO— | 2-furyl | RₐOCOO— |
| iBuOCO— | 3-furyl | RₐOCOO— |
| iBuOCO— | 2-thienyl | RₐOCOO— |
| iBuOCO— | 3-thienyl | RₐOCOO— |
| iBuOCO— | 2-pyridyl | RₐOCOO— |
| iBuOCO— | 3-pyridyl | RₐOCOO— |
| iBuOCO— | 4-pyridyl | RₐOCOO— |
| iBuOCO— | isobutenyl | RₐOCOO— |
| iBuOCO— | isopropyl | RₐOCOO— |
| iBuOCO— | cyclopropyl | RₐOCOO— |
| iBuOCO— | cyclobutyl | RₐOCOO— |
| iBuOCO— | cyclopentyl | RₐOCOO— |
| iBuOCO— | phenyl | RₐOCOO— |
| iPrOCO— | 2-furyl | RₐOCOO— |
| iPrOCO— | 3-furyl | RₐOCOO— |
| iPrOCO— | 2-thienyl | RₐOCOO— |
| iPrOCO— | 3-thienyl | RₐOCOO— |
| iPrOCO— | 2-pyridyl | RₐOCOO— |
| iPrOCO— | 3-pyridyl | RₐOCOO— |
| iPrOCO— | 4-pyridyl | RₐOCOO— |
| iPrOCO— | isobutenyl | RₐOCOO— |
| iPrOCO— | isopropyl | RₐOCOO— |
| iPrOCO— | cyclopropyl | RₐOCOO— |
| iPrOCO— | cyclobutyl | RₐOCOO— |
| iPrOCO— | cyclopentyl | RₐOCOO— |
| iPrOCO— | phenyl | RₐOCOO— |
| nPrOCO— | 2-furyl | RₐOCOO— |
| nPrOCO— | 3-furyl | RₐOCOO— |
| nPrOCO— | 2-thienyl | RₐOCOO— |
| nPrOCO— | 3-thienyl | RₐOCOO— |
| nPrOCO— | 2-pyridyl | RₐOCOO— |
| nPrOCO— | 3-pyridyl | RₐOCOO— |
| nPrOCO— | 4-pyridyl | RₐOCOO— |
| nPrOCO— | isobutenyl | RₐOCOO— |
| nPrOCO— | isopropyl | RₐOCOO— |
| nPrOCO— | cyclopropyl | RₐOCOO— |
| nPrOCO— | cyclobutyl | RₐOCOO— |
| nPrOCO— | cyclopentyl | RₐOCOO— |
| nPrOCO— | phenyl | RₐOCOO— |
| nPrCO— | 2-furyl | RₐOCOO— |
| nPrCO— | 3-furyl | RₐOCOO— |
| nPrCO— | 2-thienyl | RₐOCOO— |
| nPrCO— | 3-thienyl | RₐOCOO— |
| nPrCO— | 2-pyridyl | RₐOCOO— |
| nPrCO— | 3-pyridyl | RₐOCOO— |
| nPrCO— | 4-pyridyl | RₐOCOO— |
| nPrCO— | isobutenyl | RₐOCOO— |
| nPrCO— | isopropyl | RₐOCOO— |
| nPrCO— | cyclopropyl | RₐOCOO— |
| nPrCO— | cyclobutyl | RₐOCOO— |
| nPrCO— | cyclopentyl | RₐOCOO— |

(14)

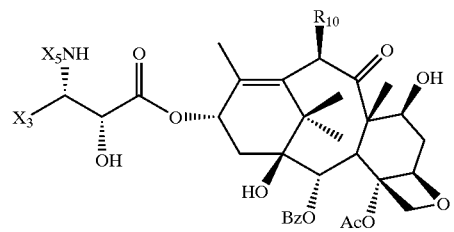

| X₅ | X₃ | R₁₀ |
|---|---|---|
| nPrCO— | phenyl | RₐOCOO— |
| tBuOCO | cyclopentyl | EtOCOO— |
| benzoyl | 3-furyl | EtOCOO— |
| benzoyl | 3-thienyl | EtOCOO— |
| benzoyl | 2-pyridyl | EtOCOO— |
| benzoyl | 3-pyridyl | EtOCOO— |
| benzoyl | 4-pyridyl | EtOCOO— |
| benzoyl | isobutenyl | EtOCOO— |
| benzoyl | isopropyl | EtOCOO— |
| benzoyl | cyclopropyl | EtOCOO— |
| benzoyl | cyclobutyl | EtOCOO— |
| benzoyl | cyclopentyl | EtOCOO— |
| benzoyl | phenyl | EtOCOO— |
| 2-FuCO— | 3-furyl | EtOCOO— |
| 2-FuCO— | 3-thienyl | EtOCOO— |
| 2-FuCO— | 2-pyridyl | EtOCOO— |
| 2-FuCO— | 3-pyridyl | EtOCOO— |
| 2-FuCO— | 4-pyridyl | EtOCOO— |
| 2-FuCO— | isobutenyl | EtOCOO— |
| 2-FuCO— | isopropyl | EtOCOO— |
| 2-FuCO— | cyclopropyl | EtOCOO— |
| 2-FuCO— | cyclobutyl | EtOCOO— |
| 2-FuCO— | cyclopentyl | EtOCOO— |
| 2-FuCO— | phenyl | EtOCOO— |
| 2-ThCO— | 3-furyl | EtOCOO— |
| 2-ThCO— | 3-thienyl | EtOCOO— |
| 2-ThCO— | 2-pyridyl | EtOCOO— |
| 2-ThCO— | 3-pyridyl | EtOCOO— |
| 2-ThCO— | 4-pyridyl | EtOCOO— |
| 2-ThCO— | isobutenyl | EtOCOO— |
| 2-ThCO— | isopropyl | EtOCOO— |
| 2-ThCO— | cyclopropyl | EtOCOO— |
| 2-ThCO— | cyclobutyl | EtOCOO— |
| 2-ThCO— | cyclopentyl | EtOCOO— |
| 2-ThCO— | phenyl | EtOCOO— |
| 2-PyCO— | 2-furyl | EtOCOO— |
| 2-PyCO— | 3-furyl | EtOCOO— |
| 2-PyCO— | 3-thienyl | EtOCOO— |
| 2-PyCO— | 2-pyridyl | EtOCOO— |
| 2-PyCO— | 3-pyridyl | EtOCOO— |
| 2-PyCO— | 4-pyridyl | EtOCOO— |
| 2-PyCO— | isobutenyl | EtOCOO— |
| 2-PyCO— | isopropyl | EtOCOO— |
| 2-PyCO— | cyclopropyl | EtOCOO— |
| 2-PyCO— | cyclobutyl | EtOCOO— |
| 2-PyCO— | cyclopentyl | EtOCOO— |
| 2-PyCO— | phenyl | EtOCOO— |
| 3PyCO— | 2-furyl | EtOCOO— |
| 3-PyCO— | 3-furyl | EtOCOO— |
| 3-PyCO— | 3-thienyl | EtOCOO— |
| 3-PyCO— | 2-pyridyl | EtOCOO— |
| 3-PyCO— | 3-pyridyl | EtOCOO— |
| 3-PyCO— | 4-pyridyl | EtOCOO— |
| 3-PyCO— | isobutenyl | EtOCOO— |
| 3-PyCO— | isopropyl | EtOCOO— |
| 3-PyCO— | cyclopropyl | EtOCOO— |
| 3-PyCO— | cyclobutyl | EtOCOO— |
| 3-PyCO— | cyclopentyl | EtOCOO— |
| 3-PyCO— | phenyl | EtOCOO— |
| 4-PyCO— | 2-furyl | EtOCOO— |
| 4-PyCO— | 3-furyl | EtOCOO— |
| 4-PyCO— | 3-thienyl | EtOCOO— |
| 4-PyCO— | 2-pyridyl | EtOCOO— |
| 4-PyCO— | 3-pyridyl | EtOCOO— |

-continued (14)

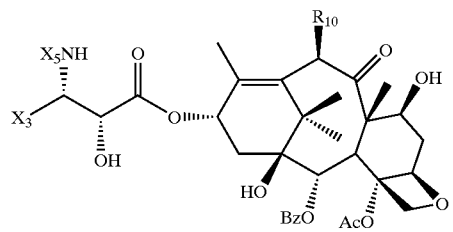

| X₅ | X₃ | R₁₀ |
|---|---|---|
| 4-PyCO— | 4-pyridyl | EtOCOO— |
| 4-PyCO— | isobutenyl | EtOCOO— |
| 4-PyCO— | isopropyl | EtOCOO— |
| 4-PyCO— | cyclopropyl | EtOCOO— |
| 4-PyCO— | cyclobutyl | EtOCOO— |
| 4-PyCO— | cyclopentyl | EtOCOO— |
| 4-PyCO— | phenyl | EtOCOO— |
| C₄H₇CO— | 3-furyl | EtOCOO— |
| C₄H₇CO— | 3-thienyl | EtOCOO— |
| C₄H₇CO— | 2-pyridyl | EtOCOO— |
| C₄H₇CO— | 3-pyridyl | EtOCOO— |
| C₄H₇CO— | 4-pyridyl | EtOCOO— |
| C₄H₇CO— | isobutenyl | EtOCOO— |
| C₄H₇CO— | isopropyl | EtOCOO— |
| C₄H₇CO— | cyclopropyl | EtOCOO— |
| C₄H₇CO— | cyclobutyl | EtOCOO— |
| C₄H₇CO— | cyclopentyl | EtOCOO— |
| C₄H₇CO— | phenyl | EtOCOO— |
| EtOCO— | 3-furyl | EtOCOO— |
| EtOCO— | 3-thienyl | EtOCOO— |
| EtOCO— | 2-pyridyl | EtOCOO— |
| EtOCO— | 3-pyridyl | EtOCOO— |
| EtOCO— | 4-pyridyl | EtOCOO— |
| EtOCO— | isobutenyl | EtOCOO— |
| EtOCO— | isopropyl | EtOCOO— |
| EtOCO— | cyclopropyl | EtOCOO— |
| EtOCO— | cyclobutyl | EtOCOO— |
| EtOCO— | cyclopentyl | EtOCOO— |
| EtOCO— | phenyl | EtOCOO— |
| ibueCO— | 2-furyl | EtOCOO— |
| ibueCO— | 3-furyl | EtOCOO— |
| ibueCO— | 2-thienyl | EtOCOO— |
| ibueCO— | 3-thienyl | EtOCOO— |
| ibueCO— | 2-pyridyl | EtOCOO— |
| ibueCO— | 3-pyridyl | EtOCOO— |
| ibueCO— | 4-pyridyl | EtOCOO— |
| ibueCO— | isobutenyl | EtOCOO— |
| ibueCO— | isopropyl | EtOCOO— |
| ibueCO— | cyclopropyl | EtOCOO— |
| ibueCO— | cyclobutyl | EtOCOO— |
| ibueCO— | cyclopentyl | EtOCOO— |
| ibueCO— | phenyl | EtOCOO— |
| iBuCO— | 2-furyl | EtOCOO— |
| iBuCO— | 3-furyl | EtOCOO— |
| iBuCO— | 2-thienyl | EtOCOO— |
| iBuCO— | 3-thienyl | EtOCOO— |
| iBuCO— | 2-pyridyl | EtOCOO— |
| iBuCO— | 3-pyridyl | EtOCOO— |
| iBuCO— | 4-pyridyl | EtOCOO— |
| iBuCO— | isobutenyl | EtOCOO— |
| iBuCO— | isopropyl | EtOCOO— |
| iBuCO— | cyclopropyl | EtOCOO— |
| iBuCO— | cyclobutyl | EtOCOO— |
| iBuCO— | cyclopentyl | EtOCOO— |
| iBuCO— | phenyl | EtOCOO— |
| iBuOCO— | 2-pyridyl | EtOCOO— |
| iBuOCO— | 3-pyridyl | EtOCOO— |
| iBuOCO— | 4-pyridyl | EtOCOO— |
| iBuOCO— | isopropyl | EtOCOO— |
| iBuOCO— | cyclobutyl | EtOCOO— |
| iBuOCO— | cyclopentyl | EtOCOO— |
| iBuOCO— | phenyl | EtOCOO— |
| iPrOCO— | 3-furyl | EtOCOO— |
| iPrOCO— | 3-thienyl | EtOCOO— |
| iPrOCO— | 2-pyridyl | EtOCOO— |
| iPrOCO— | 3-pyridyl | EtOCOO— |
| iPrOCO— | 4-pyridyl | EtOCOO— |
| iPrOCO— | isobutenyl | EtOCOO— |
| iPrOCO— | isopropyl | EtOCOO— |
| iPrOCO— | cyclopropyl | EtOCOO— |
| iPrOCO— | cyclobutyl | EtOCOO— |
| iPrOCO— | cyclopentyl | EtOCOO— |
| iPrOCO— | phenyl | EtOCOO— |
| nPrOCO— | 2-furyl | EtOCOO— |
| nPrOCO— | 3-furyl | EtOCOO— |
| nPrOCO— | 2-thienyl | EtOCOO— |
| nPrOCO— | 3-thienyl | EtOCOO— |
| nPrOCO— | 2-pyridyl | EtOCOO— |
| nPrOCO— | 3-pyridyl | EtOCOO— |
| nPrOCO— | 4-pyridyl | EtOCOO— |
| nPrOCO— | isobutenyl | EtOCOO— |
| nPrOCO— | isopropyl | EtOCOO— |
| nPrOCO— | cyclopropyl | EtOCOO— |
| nPrOCO— | cyclobutyl | EtOCOO— |
| nPrOCO— | cyclopentyl | EtOCOO— |
| nPrOCO— | phenyl | EtOCOO— |
| nPrCO— | 3-furyl | EtOCOO— |
| nPrCO— | 3-thienyl | EtOCOO— |
| nPrCO— | 2-pyridyl | EtOCOO— |
| nPrCO— | 3-pyridyl | EtOCOO— |
| nPrCO— | 4-pyridyl | EtOCOO— |
| nPrCO— | isobutenyl | EtOCOO— |
| nPrCO— | isopropyl | EtOCOO— |
| nPrCO— | cyclopropyl | EtOCOO— |
| nPrCO— | cyclobutyl | EtOCOO— |
| nPrCO— | cyclopentyl | EtOCOO— |
| nPrCO— | phenyl | EtOCOO— |
| tBuOCO | cyclopropyl | MeOCOO— |
| tBuOCO | cyclopentyl | MeOCOO— |
| benzoyl | 2-furyl | MeOCOO— |
| benzoyl | 3-furyl | MeOCOO— |
| benzoyl | 2-thienyl | MeOCOO— |
| benzoyl | 3-thienyl | MeOCOO— |
| benzoyl | 2-pyridyl | MeOCOO— |
| benzoyl | 3-pyridyl | MeOCOO— |
| benzoyl | 4-pyridyl | MeOCOO— |
| benzoyl | isobutenyl | MeOCOO— |
| benzoyl | isopropyl | MeOCOO— |
| benzoyl | cyclopropyl | MeOCOO— |
| benzoyl | cyclobutyl | MeOCOO— |
| benzoyl | cyclopentyl | MeOCOO— |
| benzoyl | phenyl | MeOCOO— |
| 2-FuCO— | 2-furyl | MeOCOO— |
| 2-FuCO— | 3-furyl | MeOCOO— |
| 2-FuCO— | 2-thienyl | MeOCOO— |
| 2-FuCO— | 3-thienyl | MeOCOO— |
| 2-FuCO— | 2-pyridyl | MeOCOO— |
| 2-FuCO— | 3-pyridyl | MeOCOO— |
| 2-FuCO— | 4-pyridyl | MeOCOO— |
| 2-FuCO— | isobutenyl | MeOCOO— |
| 2-FuCO— | isopropyl | MeOCOO— |
| 2-FuCO— | cyclopropyl | MeOCOO— |
| 2-FuCO— | cyclobutyl | MeOCOO— |
| 2-FuCO— | cyclopentyl | MeOCOO— |
| 2-FuCO— | phenyl | MeOCOO— |
| 2-ThCO— | 2-furyl | MeOCOO— |
| 2-ThCO— | 3-furyl | MeOCOO— |
| 2-ThCO— | 2-thienyl | MeOCOO— |

-continued (14)

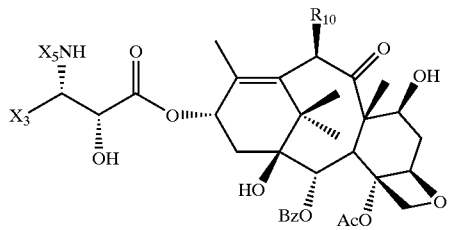

| X₅ | X₃ | R₁₀ |
|---|---|---|
| 2-ThCO— | 3-thienyl | MeOCOO— |
| 2-ThCO— | 2-pyridyl | MeOCOO— |
| 2-ThCO— | 3-pyridyl | MeOCOO— |
| 2-ThCO— | 4-pyridyl | MeOCOO— |
| 2-ThCO— | isobutenyl | MeOCOO— |
| 2-ThCO— | isopropyl | MeOCOO— |
| 2-ThCO— | cyclopropyl | MeOCOO— |
| 2-ThCO— | cyclobutyl | MeOCOO— |
| 2-ThCO— | cyclopentyl | MeOCOO— |
| 2-ThCO— | phenyl | MeOCOO— |
| 2-PyCO— | 2-furyl | MeOCOO— |
| 2-PyCO— | 3-furyl | MeOCOO— |
| 2-PyCO— | 2-thienyl | MeOCOO— |
| 2-PyCO— | 3-thienyl | MeOCOO— |
| 2-PyCO— | 2-pyridyl | MeOCOO— |
| 2-PyCO— | 3-pyridyl | MeOCOO— |
| 2-PyCO— | 4-pyridyl | MeOCOO— |
| 2-PyCO— | isobutenyl | MeOCOO— |
| 2-PyCO— | isopropyl | MeOCOO— |
| 2-PyCO— | cyclopropyl | MeOCOO— |
| 2-PyCO— | cyclobutyl | MeOCOO— |
| 2-PyCO— | cyclopentyl | MeOCOO— |
| 2-PyCO— | phenyl | MeOCOO— |
| 3PyCO— | 2-furyl | MeOCOO— |
| 3-PyCO— | 3-furyl | MeOCOO— |
| 3-PyCO— | 2-thienyl | MeOCOO— |
| 3-PyCO— | 3-thienyl | MeOCOO— |
| 3-PyCO— | 2-pyridyl | MeOCOO— |
| 3-PyCO— | 3-pyridyl | MeOCOO— |
| 3-PyCO— | 4-pyridyl | MeOCOO— |
| 3-PyCO— | isobutenyl | MeOCOO— |
| 3-PyCO— | isopropyl | MeOCOO— |
| 3-PyCO— | cyclopropyl | MeOCOO— |
| 3-PyCO— | cyclobutyl | MeOCOO— |
| 3-PyCO— | cyclopentyl | MeOCOO— |
| 3-PyCO— | phenyl | MeOCOO— |
| 4-PyCO— | 2-furyl | MeOCOO— |
| 4-PyCO— | 3-furyl | MeOCOO— |
| 4-PyCO— | 2-thienyl | MeOCOO— |
| 4-PyCO— | 3-thienyl | MeOCOO— |
| 4-PyCO— | 2-pyridyl | MeOCOO— |
| 4-PyCO— | 3-pyridyl | MeOCOO— |
| 4-PyCO— | 4-pyridyl | MeOCOO— |
| 4-PyCO— | isobutenyl | MeOCOO— |
| 4-PyCO— | isopropyl | MeOCOO— |
| 4-PyCO— | cyclopropyl | MeOCOO— |
| 4-PyCO— | cyclobutyl | MeOCOO— |
| 4-PyCO— | cyclopentyl | MeOCOO— |
| 4-PyCO— | phenyl | MeOCOO— |
| C₄H₇CO— | 2-furyl | MeOCOO— |
| C₄H₇CO— | 3-furyl | MeOCOO— |
| C₄H₇CO— | 2-thienyl | MeOCOO— |
| C₄H₇CO— | 3-thienyl | MeOCOO— |
| C₄H₇CO— | 2-pyridyl | MeOCOO— |
| C₄H₇CO— | 3-pyridyl | MeOCOO— |
| C₄H₇CO— | 4-pyridyl | MeOCOO— |
| C₄H₇CO— | isobutenyl | MeOCOO— |
| C₄H₇CO— | isopropyl | MeOCOO— |
| C₄H₇CO— | cyclopropyl | MeOCOO— |
| C₄H₇CO— | cyclobutyl | MeOCOO— |
| C₄H₇CO— | cyclopentyl | MeOCOO— |
| C₄H₇CO— | phenyl | MeOCOO— |
| EtOCO— | 2-furyl | MeOCOO— |
| EtOCO— | 3-furyl | MeOCOO— |

-continued (14)

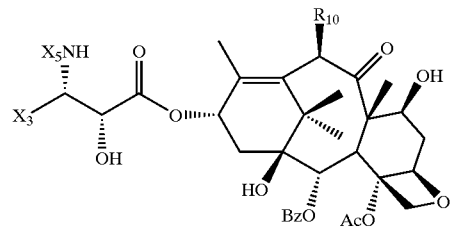

| X₅ | X₃ | R₁₀ |
|---|---|---|
| EtOCO— | 2-thienyl | MeOCOO— |
| EtOCO— | 3-thienyl | MeOCOO— |
| EtOCO— | 2-pyridyl | MeOCOO— |
| EtOCO— | 3-pyridyl | MeOCOO— |
| EtOCO— | 4-pyridyl | MeOCOO— |
| EtOCO— | isobutenyl | MeOCOO— |
| EtOCO— | isopropyl | MeOCOO— |
| EtOCO— | cyclopropyl | MeOCOO— |
| EtOCO— | cyclobutyl | MeOCOO— |
| EtOCO— | cyclopentyl | MeOCOO— |
| EtOCO— | phenyl | MeOCOO— |
| ibueCO— | 2-furyl | MeOCOO— |
| ibueCO— | 3-furyl | MeOCOO— |
| ibueCO— | 2-thienyl | MeOCOO— |
| ibueCO— | 3-thienyl | MeOCOO— |
| ibueCO— | 2-pyridyl | MeOCOO— |
| ibueCO— | 3-pyridyl | MeOCOO— |
| ibueCO— | 4-pyridyl | MeOCOO— |
| ibueCO— | isobutenyl | MeOCOO— |
| ibueCO— | isopropyl | MeOCOO— |
| ibueCO— | cyclopropyl | MeOCOO— |
| ibueCO— | cyclobutyl | MeOCOO— |
| ibueCO— | cyclopentyl | MeOCOO— |
| ibueCO— | phenyl | MeOCOO— |
| iBuCO— | 2-furyl | MeOCOO— |
| iBuCO— | 3-furyl | MeOCOO— |
| iBuCO— | 2-thienyl | MeOCOO— |
| iBuCO— | 3-thienyl | MeOCOO— |
| iBuCO— | 2-pyridyl | MeOCOO— |
| iBuCO— | 3-pyridyl | MeOCOO— |
| iBuCO— | 4-pyridyl | MeOCOO— |
| iBuCO— | isobutenyl | MeOCOO— |
| iBuCO— | isopropyl | MeOCOO— |
| iBuCO— | cyclopropyl | MeOCOO— |
| iBuCO— | cyclobutyl | MeOCOO— |
| iBuCO— | cyclopentyl | MeOCOO— |
| iBuCO— | phenyl | MeOCOO— |
| iBuOCO— | 2-furyl | MeOCOO— |
| iBuOCO— | 3-furyl | MeOCOO— |
| iBuOCO— | 2-thienyl | MeOCOO— |
| iBuOCO— | 3-thienyl | MeOCOO— |
| iBuOCO— | 2-pyridyl | MeOCOO— |
| iBuOCO— | 3-pyridyl | MeOCOO— |
| iBuOCO— | 4-pyridyl | MeOCOO— |
| iBuOCO— | isobutenyl | MeOCOO— |
| iBuOCO— | isopropyl | MeOCOO— |
| iBuOCO— | cyclopropyl | MeOCOO— |
| iBuOCO— | cyclobutyl | MeOCOO— |
| iBuOCO— | cyclopentyl | MeOCOO— |
| iBuOCO— | phenyl | MeOCOO— |
| iPrOCO— | 2-furyl | MeOCOO— |
| iPrOCO— | 3-furyl | MeOCOO— |
| iPrOCO— | 2-thienyl | MeOCOO— |
| iPrOCO— | 3-thienyl | MeOCOO— |
| iPrOCO— | 2-pyridyl | MeOCOO— |
| iPrOCO— | 3-pyridyl | MeOCOO— |
| iPrOCO— | 4-pyridyl | MeOCOO— |
| iPrOCO— | isobutenyl | MeOCOO— |
| iPrOCO— | isopropyl | MeOCOO— |
| iPrOCO— | cyclopropyl | MeOCOO— |
| iPrOCO— | cyclobutyl | MeOCOO— |
| iPrOCO— | cyclopentyl | MeOCOO— |
| iPrOCO— | phenyl | MeOCOO— |
| nPrOCO— | 2-furyl | MeOCOO— |

-continued (14)

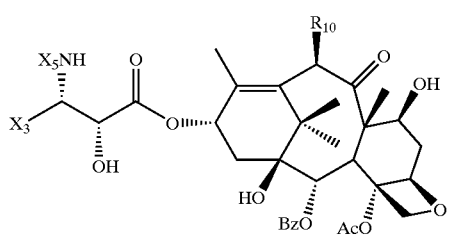

| X$_5$ | X$_3$ | R$_{10}$ |
|---|---|---|
| nPrOCO— | 3-furyl | MeOCOO— |
| nPrOCO— | 2-thienyl | MeOCOO— |
| nPrOCO— | 3-thienyl | MeOCOO— |
| nPrOCO— | 2-pyridyl | MeOCOO— |
| nPrOCO— | 3-pyridyl | MeOCOO— |
| nPrOCO— | 4-pyridyl | MeOCOO— |
| nPrOCO— | isobutenyl | MeOCOO— |
| nPrOCO— | isopropyl | MeOCOO— |
| nPrOCO— | cyclopropyl | MeOCOO— |
| nPrOCO— | cyclobutyl | MeOCOO— |
| nPrOCO— | cyclopentyl | MeOCOO— |
| nPrOCO— | phenyl | MeOCOO— |
| nPrCO— | 2-furyl | MeOCOO— |
| nPrCO— | 3-furyl | MeOCOO— |
| nPrCO— | 2-thienyl | MeOCOO— |
| nPrCO— | 3-thienyl | MeOCOO— |
| nPrCO— | 2-pyridyl | MeOCOO— |
| nPrCO— | 3-pyridyl | MeOCOO— |
| nPrCO— | 4-pyridyl | MeOCOO— |
| nPrCO— | isobutenyl | MeOCOO— |
| nPrCO— | isopropyl | MeOCOO— |
| nPrCO— | cyclopropyl | MeOCOO— |
| nPrCO— | cyclobutyl | MeOCOO— |
| nPrCO— | cyclopentyl | MeOCOO— |
| nPrCO— | phenyl | MeOCOO— |

EXAMPLE 4

Following the processes described in Example 1 and elsewhere herein, the following specific taxanes having structural formula 15 may be prepared, wherein in each of the series (that is, each of series "A" through "K") $R_7$ is hydroxy and $R_{10}$ is as previously defined, including wherein $R_{10}$ is $R_{10a}OCOO$— and $R_{10a}$ is (i) substituted or unsubstituted, preferably unsubstituted, $C_2$ to $C_8$ alkyl (straight, branched or cyclic), such as ethyl, propyl, butyl, pentyl, or hexyl; (ii) substituted or unsubstituted, preferably unsubstituted, $C_2$ to $C_8$ alkenyl (straight, branched or cyclic), such as ethenyl, propenyl, butenyl, pentenyl or hexenyl; (iii) substituted or unsubstituted, preferably unsubstituted, $C_2$ to $C_8$ alkynyl (straight or branched) such as ethynyl, propynyl, butynyl, pentynyl, or hexynyl; (iv) substituted or unsubstituted, preferably unsubstituted, phenyl; or (v) substituted or unsubstituted, preferably unsubstituted, heteroaromatic such as furyl, thienyl, or pyridyl.

In the "A" series of compounds, $X_{10}$ is as otherwise as defined herein. Preferably, heterocyclo is substituted or unsubstituted furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_2$, is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each of $X_3$, $X_5$, $R_2$, $R_9$ and $R_{10}$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(15)

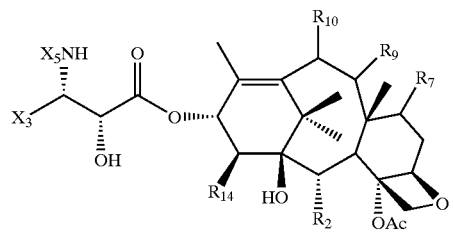

| Series | $X_5$ | $X_3$ | $R_{10}$ | $R_2$ | $R_9$ | $R_{14}$ |
|---|---|---|---|---|---|---|
| A1 | —COOX$_{10}$ | heterocyclo | $R_{10a}$OCOO— | $C_6H_5$COO— | O | H |
| A2 | —COX$_{10}$ | heterocyclo | $R_{10a}$OCOO— | $C_6H_5$COO— | O | H |
| A3 | —CONHX$_{10}$ | heterocyclo | $R_{10a}$OCOO— | $C_6H_5$COO— | O | H |
| A4 | —COOX$_{10}$ | optionally substituted $C_2$ to $C_8$ alkyl | $R_{10a}$OCOO— | $C_6H_5$COO— | O | H |
| A5 | —COX$_{10}$ | optionally substituted $C_2$ to $C_8$ alkyl | $R_{10a}$OCOO— | $C_6H_5$COO— | O | H |
| A6 | —CONHX$_{10}$ | optionally substituted $C_2$ to $C_8$ alkyl | $R_{10a}$OCOO— | $C_6H_5$COO— | O | H |
| A7 | —COOX$_{10}$ | optionally substituted $C_2$ to $C_8$ alkenyl | $R_{10a}$OCOO— | $C_6H_5$COO— | O | H |
| A8 | —COX$_{10}$ | optionally substituted $C_2$ to $C_8$ alkenyl | $R_{10a}$OCOO— | $C_6H_5$COO— | O | H |
| A9 | —CONHX$_{10}$ | optionally substituted $C_2$ to $C_8$ alkenyl | $R_{10a}$OCOO— | $C_6H_5$COO— | O | H |
| A10 | —COOX$_{10}$ | optionally substituted $C_2$ to $C_8$ alkynyl | $R_{10a}$OCOO— | $C_6H_5$COO— | O | H |
| A11 | —COX$_{10}$ | optionally substituted $C_2$ to $C_8$ alkynyl | $R_{10a}$OCOO— | $C_6H_5$COO— | O | H |
| A12 | —CONHX$_{10}$ | optionally substituted $C_2$ to $C_8$ alkynyl | $R_{10a}$OCOO— | $C_6H_5$COO— | O | H |
| B1 | —COOX$_{10}$ | heterocyclo | $R_{10a}$OCOO— | $R_{2a}$COO— | O | H |
| B2 | —COX$_{10}$ | heterocyclo | $R_{10a}$OCOO— | $R_{2a}$COO— | O | H |
| B3 | —CONHX$_{10}$ | heterocyclo | $R_{10a}$OCOO— | $R_{2a}$COO— | O | H |
| B4 | —COOX$_{10}$ | optionally substituted $C_2$ to $C_8$ alkyl | $R_{10a}$OCOO— | $R_{2a}$COO— | O | H |
| B5 | —COX$_{10}$ | optionally substituted $C_2$ to $C_8$ alkyl | $R_{10a}$OCOO— | $R_{2a}$COO— | O | H |
| B6 | —CONHX$_{10}$ | optionally substituted $C_2$ to $C_8$ alkyl | $R_{10a}$OCOO— | $R_{2a}$COO— | O | H |
| B7 | —COOX$_{10}$ | optionally substituted $C_2$ to $C_8$ alkenyl | $R_{10a}$OCOO— | $R_{2a}$COO— | O | H |
| B8 | —COX$_{10}$ | optionally substituted $C_2$ to $C_8$ alkenyl | $R_{10a}$OCOO— | $R_{2a}$COO— | O | H |
| B9 | —CONHX$_{10}$ | optionally substituted $C_2$ to $C_8$ alkenyl | $R_{10a}$OCOO— | $R_{2a}$COO— | O | H |
| B10 | —COOX$_{10}$ | optionally substituted $C_2$ to $C_8$ alkynyl | $R_{10a}$OCOO— | $R_{2a}$COO— | O | H |
| B11 | —COX$_{10}$ | optionally substituted $C_2$ to $C_8$ alkynyl | $R_{10a}$OCOO— | $R_{2a}$COO— | O | H |
| B12 | —CONHX$_{10}$ | optionally substituted $C_2$ to $C_8$ alkynyl | $R_{10a}$OCOO— | $R_{2a}$COO— | O | H |
| C1 | —COOX$_{10}$ | heterocyclo | $R_{10a}$OCOO— | $C_6H_5$COO— | $R_{9a}$COO— | H |
| C2 | —COX$_{10}$ | heterocyclo | $R_{10a}$OCOO— | $C_6H_5$COO— | $R_{9a}$COO— | H |
| C3 | —CONHX$_{10}$ | heterocyclo | $R_{10a}$OCOO— | $C_6H_5$COO— | $R_{9a}$COO— | H |
| C4 | —COOX$_{10}$ | optionally substituted $C_2$ to $C_8$ alkyl | $R_{10a}$OCOO— | $C_6H_5$COO— | $R_{9a}$COO— | H |
| C5 | —COX$_{10}$ | optionally substituted $C_2$ to $C_8$ alkyl | $R_{10a}$OCOO— | $C_6H_5$COO— | $R_{9a}$COO— | H |
| C6 | —CONHX$_{10}$ | optionally substituted $C_2$ to $C_8$ alkyl | $R_{10a}$OCOO— | $C_6H_5$COO— | $R_{9a}$COO— | H |
| C7 | —COOX$_{10}$ | optionally substituted $C_2$ to $C_8$ alkenyl | $R_{10a}$OCOO— | $C_6H_5$COO— | $R_{9a}$COO— | H |
| C8 | —COX$_{10}$ | optionally substituted $C_2$ to $C_8$ alkenyl | $R_{10a}$OCOO— | $C_6H_5$COO— | $R_{9a}$COO— | H |
| C9 | —CONHX$_{10}$ | optionally substituted $C_2$ to $C_8$ alkenyl | $R_{10a}$OCOO— | $C_6H_5$COO— | $R_{9a}$COO— | H |

-continued (15)

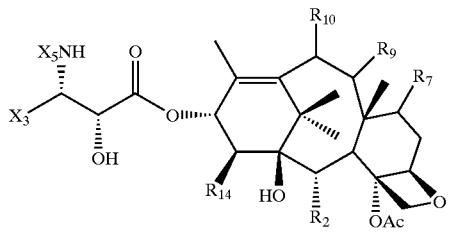

| Series | $X_5$ | $X_3$ | $R_{10}$ | $R_2$ | $R_9$ | $R_{14}$ |
|---|---|---|---|---|---|---|
| C10 | —COOX$_{10}$ | optionally substituted C$_2$ to C$_8$ alkynyl | R$_{10a}$OCOO— | C$_6$H$_5$COO— | R$_{9a}$COO— | H |
| C11 | —COX$_{10}$ | optionally substituted C$_2$ to C$_8$ alkynyl | R$_{10a}$OCOO— | C$_6$H$_5$COO— | R$_{9a}$COO— | H |
| C12 | —CONHX$_{10}$ | optionally substituted C$_2$ to C$_8$ alkynyl | R$_{10a}$OCOO— | C$_6$H$_5$COO— | R$_{9a}$COO— | H |
| D1 | —COOX$_{10}$ | heterocyclo | R$_{10a}$OCOO— | C$_6$H$_5$COO— | OH | H |
| D2 | —COX$_{10}$ | heterocyclo | R$_{10a}$OCOO— | C$_6$H$_5$COO— | OH | H |
| D3 | —CONHX$_{10}$ | heterocyclo | R$_{10a}$OCOO— | C$_6$H$_5$COO— | OH | H |
| D4 | —COOX$_{10}$ | optionally substituted C$_2$ to C$_8$ alkyl | R$_{10a}$OCOO— | C$_6$H$_5$COO— | OH | H |
| D5 | —COX$_{10}$ | optionally substituted C$_2$ to C$_8$ alkyl | R$_{10a}$OCOO— | C$_6$H$_5$COO— | OH | H |
| D6 | —CONHX$_{10}$ | optionally substituted C$_2$ to C$_8$ alkyl | R$_{10a}$OCOO— | C$_6$H$_5$COO— | OH | H |
| D7 | —COOX$_{10}$ | optionally substituted C$_2$ to C$_8$ alkenyl | R$_{10a}$OCOO— | C$_6$H$_5$COO— | OH | H |
| D8 | —COX$_{10}$ | optionally substituted C$_2$ to C$_8$ alkenyl | R$_{10a}$OCOO— | C$_6$H$_5$COO— | OH | H |
| D9 | —CONHX$_{10}$ | optionally substituted C$_2$ to C$_8$ alkenyl | R$_{10a}$OCOO— | C$_6$H$_5$COO— | OH | H |
| D10 | —COOX$_{10}$ | optionally substituted C$_2$ to C$_8$ alkynyl | R$_{10a}$OCOO— | C$_6$H$_5$COO— | OH | H |
| D11 | —COX$_{10}$ | optionally substituted C$_2$ to C$_8$ alkynyl | R$_{10a}$OCOO— | C$_6$H$_5$COO— | OH | H |
| D12 | —CONHX$_{10}$ | optionally substituted C$_2$ to C$_8$ alkynyl | R$_{10a}$OCOO— | C$_6$H$_5$COO— | OH | H |
| E1 | —COOX$_{10}$ | heterocyclo | R$_{10a}$OCOO— | C$_6$H$_5$COO— | O | OH |
| E2 | —COX$_{10}$ | heterocyclo | R$_{10a}$OCOO— | C$_6$H$_5$COO— | O | OH |
| E3 | —CONHX$_{10}$ | heterocyclo | R$_{10a}$OCOO— | C$_6$H$_5$COO— | O | OH |
| E4 | —COOX$_{10}$ | optionally substituted C$_2$ to C$_8$ alkyl | R$_{10a}$OCOO— | C$_6$H$_5$COO— | O | OH |
| E5 | —COX$_{10}$ | optionally substituted C$_2$ to C$_8$ alkyl | R$_{10a}$OCOO— | C$_6$H$_5$COO— | O | OH |
| E6 | —CONHX$_{10}$ | optionally substituted C$_2$ to C$_8$ alkyl | R$_{10a}$OCOO— | C$_6$H$_5$COO— | O | OH |
| E7 | —COOX$_{10}$ | optionally substituted C$_2$ to C$_8$ alkenyl | R$_{10a}$OCOO— | C$_6$H$_5$COO— | O | OH |
| E8 | —COX$_{10}$ | optionally substituted C$_2$ to C$_8$ alkenyl | R$_{10a}$OCOO— | C$_6$H$_5$COO— | O | OH |
| E9 | —CONHX$_{10}$ | optionally substituted C$_2$ to C$_8$ alkenyl | R$_{10a}$OCOO— | C$_6$H$_5$COO— | O | OH |
| E10 | —COOX$_{10}$ | optionally substituted C$_2$ to C$_8$ alkynyl | R$_{10a}$OCOO— | C$_6$H$_5$COO— | O | OH |
| E11 | —COX$_{10}$ | optionally substituted C$_2$ to C$_8$ alkynyl | R$_{10a}$OCOO— | C$_6$H$_5$COO— | O | OH |
| E12 | —CONHX$_{10}$ | optionally substituted C$_2$ to C$_8$ alkynyl | R$_{10a}$OCOO— | C$_6$H$_5$COO— | O | OH |
| F1 | —COOX$_{10}$ | heterocyclo | R$_{10a}$OCOO— | R$_{2a}$COO— | R$_{9a}$COO— | H |
| F2 | —COX$_{10}$ | heterocyclo | R$_{10a}$OCOO— | R$_{2a}$COO— | R$_{9a}$COO— | H |
| F3 | —CONHX$_{10}$ | heterocyclo | R$_{10a}$OCOO— | R$_{2a}$COO— | R$_{9a}$COO— | H |
| F4 | —COOX$_{10}$ | optionally substituted C$_2$ to C$_8$ alkyl | R$_{10a}$OCOO— | R$_{2a}$COO— | R$_{9a}$COO— | H |
| F5 | —COX$_{10}$ | optionally substituted C$_2$ to C$_8$ alkyl | R$_{10a}$OCOO— | R$_{2a}$COO— | R$_{9a}$COO— | H |
| F6 | —CONHX$_{10}$ | optionally substituted C$_2$ to C$_8$ alkyl | R$_{10a}$OCOO— | R$_{2a}$COO— | R$_{9a}$COO— | H |
| F7 | —COOX$_{10}$ | optionally substituted C$_2$ to C$_8$ alkenyl | R$_{10a}$OCOO— | R$_{2a}$COO— | R$_{9a}$COO— | H |
| F8 | —COX$_{10}$ | optionally substituted C$_2$ to C$_8$ alkenyl | R$_{10a}$OCOO— | R$_{2a}$COO— | R$_{9a}$COO— | H |
| F9 | —CONHX$_{10}$ | optionally substituted C$_2$ to C$_8$ alkenyl | R$_{10a}$OCOO— | R$_{2a}$COO— | R$_{9a}$COO— | H |

-continued (15)

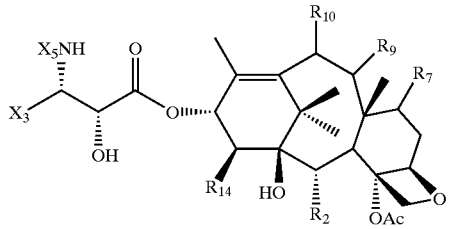

| Series | X₅ | X₃ | R₁₀ | R₂ | R₉ | R₁₄ |
|---|---|---|---|---|---|---|
| F10 | —COOX₁₀ | optionally substituted C₂ to C₈ alkynyl | R₁₀ₐOCOO— | R₂ₐCOO— | R₉ₐCOO— | H |
| F11 | —COX₁₀ | optionally substituted C₂ to C₈ alkynyl | R₁₀ₐOCOO— | R₂ₐCOO— | R₉ₐCOO— | H |
| F12 | —CONHX₁₀ | optionally substituted C₂ to C₈ alkynyl | R₁₀ₐOCOO— | R₂ₐCOO— | R₉ₐCOO— | H |
| G1 | —COOX₁₀ | heterocyclo | R₁₀ₐOCOO— | R₂ₐCOO— | OH | H |
| G2 | —COX₁₀ | heterocyclo | R₁₀ₐOCOO— | R₂ₐCOO— | OH | H |
| G3 | —CONHX₁₀ | heterocyclo | R₁₀ₐOCOO— | R₂ₐCOO— | OH | H |
| G4 | —COOX₁₀ | optionally substituted C₂ to C₈ alkyl | R₁₀ₐOCOO— | R₂ₐCOO— | OH | H |
| G5 | —COX₁₀ | optionally substituted C₂ to C₈ alkyl | R₁₀ₐOCOO— | R₂ₐCOO— | OH | H |
| G6 | —CONHX₁₀ | optionally substituted C₂ to C₈ alkyl | R₁₀ₐOCOO— | R₂ₐCOO— | OH | H |
| G7 | —COOX₁₀ | optionally substituted C₂ to C₈ alkenyl | R₁₀ₐOCOO— | R₂ₐCOO— | OH | H |
| G8 | —COX₁₀ | optionally substituted C₂ to C₈ alkenyl | R₁₀ₐOCOO— | R₂ₐCOO— | OH | H |
| G9 | —CONHX₁₀ | optionally substituted C₂ to C₈ alkenyl | R₁₀ₐOCOO— | R₂ₐCOO— | OH | H |
| G10 | —COOX₁₀ | optionally substituted C₂ to C₈ alkynyl | R₁₀ₐOCOO— | R₂ₐCOO— | OH | H |
| G11 | —COX₁₀ | optionally substituted C₂ to C₈ alkynyl | R₁₀ₐOCOO— | R₂ₐCOO— | OH | H |
| G12 | —CONHX₁₀ | optionally substituted C₂ to C₈ alkynyl | R₁₀ₐOCOO— | R₂ₐCOO— | OH | H |
| H1 | —COOX₁₀ | heterocyclo | R₁₀ₐOCOO— | C₆H₅COO— | OH | OH |
| H2 | —COX₁₀ | heterocyclo | R₁₀ₐOCOO— | C₆H₅COO— | OH | OH |
| H3 | —CONHX₁₀ | heterocyclo | R₁₀ₐOCOO— | C₆H₅COO— | OH | OH |
| H4 | —COOX₁₀ | optionally substituted C₂ to C₈ alkyl | R₁₀ₐOCOO— | C₆H₅COO— | OH | OH |
| H5 | —COX₁₀ | optionally substituted C₂ to C₈ alkyl | R₁₀ₐOCOO— | C₆H₅COO— | OH | OH |
| H6 | —CONHX₁₀ | optionally substituted C₂ to C₈ alkyl | R₁₀ₐOCOO— | C₆H₅COO— | OH | OH |
| H7 | —COOX₁₀ | optionally substituted C₂ to C₈ alkenyl | R₁₀ₐOCOO— | C₆H₅COO— | OH | OH |
| H8 | —COX₁₀ | optionally substituted C₂ to C₈ alkenyl | R₁₀ₐOCOO— | C₆H₅COO— | OH | OH |
| H9 | —CONHX₁₀ | optionally substituted C₂ to C₈ alkenyl | R₁₀ₐOCOO— | C₆H₅COO— | OH | OH |
| H10 | —COOX₁₀ | optionally substituted C₂ to C₈ alkynyl | R₁₀ₐOCOO— | C₆H₅COO— | OH | OH |
| H11 | —COX₁₀ | optionally substituted C₂ to C₈ alkynyl | R₁₀ₐOCOO— | C₆H₅COO— | OH | OH |
| H12 | —CONHX₁₀ | optionally substituted C₂ to C₈ alkynyl | R₁₀ₐOCOO— | C₆H₅COO— | OH | OH |
| I1 | —COOX₁₀ | heterocyclo | R₁₀ₐOCOO— | R₂ₐCOO— | O | OH |
| I2 | —COX₁₀ | heterocyclo | R₁₀ₐOCOO— | R₂ₐCOO— | O | OH |
| I3 | —CONHX₁₀ | heterocyclo | R₁₀ₐOCOO— | R₂ₐCOO— | O | OH |
| I4 | —COOX₁₀ | optionally substituted C₂ to C₈ alkyl | R₁₀ₐOCOO— | R₂ₐCOO— | O | OH |
| I5 | —COX₁₀ | optionally substituted C₂ to C₈ alkyl | R₁₀ₐOCOO— | R₂ₐCOO— | O | OH |
| I6 | —CONHX₁₀ | optionally substituted C₂ to C₈ alkyl | R₁₀ₐOCOO— | R₂ₐCOO— | O | OH |
| I7 | —COOX₁₀ | optionally substituted C₂ to C₈ alkenyl | R₁₀ₐOCOO— | R₂ₐCOO— | O | OH |
| I8 | —COX₁₀ | optionally substituted C₂ to C₈ alkenyl | R₁₀ₐOCOO— | R₂ₐCOO— | O | OH |
| I9 | —CONHX₁₀ | optionally substituted C₂ to C₈ alkenyl | R₁₀ₐOCOO— | R₂ₐCOO— | O | OH |

-continued (15)

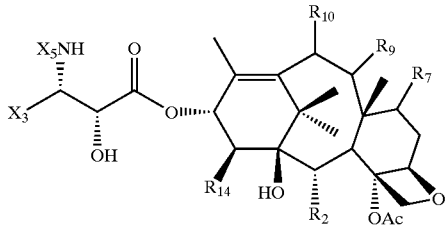

| Series | $X_5$ | $X_3$ | $R_{10}$ | $R_2$ | $R_9$ | $R_{14}$ |
|---|---|---|---|---|---|---|
| I10 | —COOX$_{10}$ | optionally substituted C$_2$ to C$_8$ alkynyl | R$_{10a}$OCOO— | R$_{2a}$COO— | O | OH |
| I11 | —COX$_{10}$ | optionally substituted C$_2$ to C$_8$ alkynyl | R$_{10a}$OCOO— | R$_{2a}$COO— | O | OH |
| I12 | —CONHX$_{10}$ | optionally substituted C$_2$ to C$_8$ alkynyl | R$_{10a}$OCOO— | R$_{2a}$COO— | O | OH |
| J1 | —COOX$_{10}$ | heterocyclo | R$_{10a}$OCOO— | R$_{2a}$COO— | OH | OH |
| J2 | —COX$_{10}$ | heterocyclo | R$_{10a}$OCOO— | R$_{2a}$COO— | OH | OH |
| J3 | —CONHX$_{10}$ | heterocyclo | R$_{10a}$OCOO— | R$_{2a}$COO— | OH | OH |
| J4 | —COOX$_{10}$ | optionally substituted C$_2$ to C$_8$ alkyl | R$_{10a}$OCOO— | R$_{2a}$COO— | OH | OH |
| J5 | —COX$_{10}$ | optionally substituted C$_2$ to C$_8$ alkyl | R$_{10a}$OCOO— | R$_{2a}$COO— | OH | OH |
| J6 | —CONHX$_{10}$ | optionally substituted C$_2$ to C$_8$ alkyl | R$_{10a}$OCOO— | R$_{2a}$COO— | OH | OH |
| J7 | —COOX$_{10}$ | optionally substituted C$_2$ to C$_8$ alkenyl | R$_{10a}$OCOO— | R$_{2a}$COO— | OH | OH |
| J8 | —COX$_{10}$ | optionally substituted C$_2$ to C$_8$ alkenyl | R$_{10a}$OCOO— | R$_{2a}$COO— | OH | OH |
| J9 | —CONHX$_{10}$ | optionally substituted C$_2$ to C$_8$ alkenyl | R$_{10a}$OCOO— | R$_{2a}$COO— | OH | OH |
| J10 | —COOX$_{10}$ | optionally substituted C$_2$ to C$_8$ alkynyl | R$_{10a}$OCOO— | R$_{2a}$COO— | OH | OH |
| J11 | —COX$_{10}$ | optionally substituted C$_2$ to C$_8$ alkynyl | R$_{10a}$OCOO— | R$_{2a}$COO— | OH | OH |
| J12 | —CONHX$_{10}$ | optionally substituted C$_2$ to C$_8$ alkynyl | R$_{10a}$OCOO— | R$_{2a}$COO— | OH | OH |
| K1 | —COOX$_{10}$ | heterocyclo | R$_{10a}$OCOO— | R$_{2a}$COO— | R$_{9a}$COO— | OH |
| K2 | —COX$_{10}$ | heterocyclo | R$_{10a}$OCOO— | R$_{2a}$COO— | R$_{9a}$COO— | OH |
| K3 | —CONHX$_{10}$ | heterocyclo | R$_{10a}$OCOO— | R$_{2a}$COO— | R$_{9a}$COO— | OH |
| K4 | —COOX$_{10}$ | optionally substituted C$_2$ to C$_8$ alkyl | R$_{10a}$OCOO— | R$_{2a}$COO— | R$_{9a}$COO— | OH |
| K5 | —COX$_{10}$ | optionally substituted C$_2$ to C$_8$ alkyl | R$_{10a}$OCOO— | R$_{2a}$COO— | R$_{9a}$COO— | OH |
| K6 | —CONHX$_{10}$ | optionally substituted C$_2$ to C$_8$ alkyl | R$_{10a}$OCOO— | R$_{2a}$COO— | R$_{9a}$COO— | OH |
| K7 | —COOX$_{10}$ | optionally substituted C$_2$ to C$_8$ alkenyl | R$_{10a}$OCOO— | R$_{2a}$COO— | R$_{9a}$COO— | OH |
| K8 | —COX$_{10}$ | optionally substituted C$_2$ to C$_8$ alkenyl | R$_{10a}$OCOO— | R$_{2a}$COO— | R$_{9a}$COO— | OH |
| K9 | —CONHX$_{10}$ | optionally substituted C$_2$ to C$_8$ alkenyl | R$_{10a}$OCOO— | R$_{2a}$COO— | R$_{9a}$COO— | OH |
| K10 | —COOX$_{10}$ | optionally substituted C$_2$ to C$_8$ alkynyl | R$_{10a}$OCOO— | R$_{2a}$COO— | R$_{9a}$COO— | OH |
| K11 | —COX$_{10}$ | optionally substituted C$_2$ to C$_8$ alkynyl | R$_{10a}$OCOO— | R$_{2a}$COO— | R$_{9a}$COO— | OH |
| K12 | —CONHX$_{10}$ | optionally substituted C$_2$ to C$_8$ alkynyl | R$_{10a}$OCOO— | R$_{2a}$COO— | R$_{9a}$COO— | OH |

EXAMPLE 5

In Vitro Cytotoxicity Measured by the Cell Colony Formation Assay

Four hundred cells (HCT116) were plated in 60 mm Petri dishes containing 2.7 mL of medium (modified McCoy's 5a medium containing 10% fetal bovine serum and 100 units/ mL penicillin and 100 g/mL streptomycin). The cells were incubated in a CO$_2$ incubator at 37° C. for 5 h for attachment to the bottom of Petri dishes. The compounds identified in Example 2 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 1755 | <1 |
| 1767 | <10 |
| 1781 | <1 |
| 1799 | <1 |
| 1808 | <10 |
| 1811 | <1 |
| 1822 | <1 |
| 1838 | <1 |
| 1841 | <1 |
| 1855 | <10 |
| 1867 | <1 |
| 1999 | <1 |
| 2002 | <1 |
| 2011 | <10 |
| 2020 | <1 |
| 2032 | <1 |
| 2044 | <1 |
| 2050 | <1 |
| 2062 | <10 |
| 2077 | <10 |
| 2086 | <1 |
| 2097 | <1 |
| 2666 | <1 |
| 2972 | <10 |
| 2988 | <1 |
| 2999 | <1 |
| 3003 | <10 |
| 3011 | <1 |
| 3020 | <1 |
| 3033 | <10 |
| 3155 | <1 |
| 3181 | <1 |
| 3243 | <1 |
| 3300 | <10 |
| 3393 | >50 |
| 3433 | 22.3 |
| 3911 | <1 |
| 3929 | <1 |
| 3963 | <1 |
| 4000 | <1 |
| 4020 | <1 |
| 4074 | <1 |
| 4088 | <10 |
| 4090 | <1 |
| 4374 | <1 |
| 4636 | <10 |
| 6466 | <10 |
| 4959 | <1 |
| 4924 | <10 |
| 4844 | <1 |
| 5171 | <1 |
| 5155 | <10 |
| 1788 | <1 |
| 1767 | <10 |
| 1771 | <10 |
| 1866 | <1 |
| 2060 | <10 |
| 2092 | <1 |
| 2088 | <1 |

EXAMPLE 6

Preparation of Solutions for Oral Administration

Solution 1: Antitumor compound 1771 was dissolved in ethanol to form a solution containing 145 mg of the compound per ml of solution. An equal volume of Cremophor® EL solution was added to the solution while stirring to form a solution containing 72.5 mg of compound 1771 per ml of solution. This solution was diluted using 9 parts by weight of saline to form a pharmaceutically acceptable solution for administration to a patient.

Solution 2: Antitumor compound 1781 was dissolved in ethanol to form a solution containing 98 mg of the compound per ml of solution. An equal volume of Cremophor® EL was added to the solution while stirring to form an solution containing 49 mg of compound 1781 per ml of solution. This solution was diluted using 9 parts by weight of saline to form a pharmaceutically acceptable solution for administration to a patient.

What is claimed is:

1. A taxane having the formula:

wherein
$R_2$ is acyloxy;
$R_7$ is hydroxy;
$R_9$ is keto, hydroxy, or acyloxy;
$R_{10}$ is carbonate;
$R_{14}$ is hydrido or hydroxy;
$X_3$ is substituted or unsubstituted heterocyclo;
$X_5$ is —$COX_{10}$, —$COOX_{10}$, or —$CONHX_{10}$;
$X_{10}$ is hydrocarbyl, substituted hydrocarbyl, or heterocyclo; and
Ac is acetyl.

2. The taxane of claim 1 wherein $R_{10}$ is $R_{10a}$OCOO— and $R_{10a}$ is substituted or unsubstituted $C_1$-$C_8$ alkyl, $C_2$-$C_8$ alkenyl or $C_2$-$C_8$ alkynyl.

3. The taxane of claim 2 wherein $X_3$ is furyl, thienyl or pyridyl.

4. The taxane of claim 2 wherein $X_5$ is —$COX_{10}$ and $X_{10}$ is phenyl, or $X_5$ is —$COOX_{10}$ and $X_{10}$ is t-butyl.

5. The taxane of claim 2 wherein $R_{14}$ is hydrido.

6. The taxane of claim 5 wherein $X_3$ is furyl, thienyl or pyridyl.

7. The taxane of claim 5 wherein $X_5$ is —$COX_{10}$ and $X_{10}$ is phenyl, or $X_5$ is —$COOX_{10}$ and $X_{10}$ is t-butyl.

8. The taxane of claim 2 wherein $R_2$ is benzoyloxy.

9. The taxane of claim 8 wherein $X_3$ is furyl, thienyl or pyridyl.

10. The taxane of claim 8 wherein $X_5$ is —$COX_{10}$ and $X_{10}$ is phenyl, or $X_5$ is —$COOX_{10}$ and $X_{10}$ is t-butyl.

11. The taxane of claim 2 wherein $R_{14}$ is hydrido and $R_9$ is keto.

12. The taxane of claim 11 wherein $X_3$ is 2-furyl, 3-furyl, 2-thienyl, 3-thienyl, 2-pyridyl, 3-pyridyl or 4-pyridyl.

13. The taxane of claim 11 wherein $X_5$ is —$COX_{10}$ and $X_{10}$ is phenyl, or $X_5$ is —$COOX_{10}$ and $X_{10}$ is t-butyl.

14. The taxane of claim 2 wherein $R_2$ is benzoyloxy and $R_9$ is keto.

15. The taxane of claim 14 wherein $X_3$ is 2-furyl, 3-furyl, 2-thienyl, 3-thienyl, 2-pyridyl, 3-pyridyl or 4-pyridyl.

16. The taxane of claim 14 wherein $X_5$ is —$COX_{10}$ and $X_{10}$ is phenyl, or $X_5$ is —$COOX_{10}$ and $X_{10}$ is t-butyl.

17. The taxane of claim 2 wherein $R_{14}$ is hydrido and $R_2$ is benzoyloxy.

18. The taxane of claim 17 wherein $X_3$ is 2-furyl, 3-furyl, 2-thienyl, 3-thienyl, 2-pyridyl, 3-pyridyl or 4-pyridyl.

19. The taxane of claim 17 wherein $X_5$ is —$COX_{10}$ and $X_{10}$ is phenyl, or $X_5$ is —$COOX_{10}$ and $X_{10}$ is t-butyl.

20. The taxane of claim 2 wherein $R_{14}$ is hydrido, $R_9$ is keto, and $R_2$ is benzoyloxy.

21. The taxane of claim 20 wherein $X_3$ is 2-furyl, 3-furyl, 2-thienyl, 3-thienyl, 2-pyridyl, 3-pyridyl or 4-pyridyl.

22. The taxane of claim 20 wherein $X_5$ is —$COX_{10}$ and $X_{10}$ is phenyl, or $X_5$ is —$COOX_{10}$ and $X_{10}$ is t-butyl.

23. The taxane of claim 1 wherein $R_{10}$ is $R_{10a}OCOO$— and $R_{10a}$ is $C_1$–$C_8$ alkyl.

24. The taxane of claim 23 wherein $X_3$ is 2-furyl, 3-furyl, 2-thienyl, 3-thienyl, 2-pyridyl, 3-pyridyl or 4-pyridyl.

25. The taxane of claim 23 wherein $X_5$ is —$COX_{10}$ and $X_{10}$ is phenyl, or $X_5$ is —$COOX_{10}$ and $X_{10}$ is t-butyl.

26. The taxane of claim 23 wherein $R_{14}$ is hydrido.

27. The taxane of claim 26 wherein $X_3$ is 2-furyl, 3-furyl, 2-thienyl, 3-thienyl, 2-pyridyl, 3-pyridyl or 4-pyridyl.

28. The taxane of claim 26 wherein $X_5$ is —$COX_{10}$ and $X_{10}$ is phenyl, or $X_5$ is —$COOX_{10}$ and $X_{10}$ is t-butyl.

29. The taxane of claim 23 wherein $R_2$ is benzoyloxy.

30. The taxane of claim 29 wherein $X_3$ is 2-furyl, 3-furyl, 2-thienyl, 3-thienyl, 2-pyridyl, 3-pyridyl or 4-pyridyl.

31. The taxane of claim 29 wherein $X_5$ is —$COX_{10}$ and $X_{10}$ is phenyl, or $X_5$ is —$COOX_{10}$ and $X_{10}$ is t-butyl.

32. The taxane of claim 23 wherein $R_{14}$ is hydrido, $R_9$ is keto, and $R_2$ is benzoyloxy.

33. The taxane of claim 32 wherein $X_3$ is 2-furyl, 3-furyl, 2-thienyl, 3-thienyl, 2-pyridyl, 3-pyridyl or 4-pyridyl.

34. The taxane of claim 32 wherein $X_5$ is —$COX_{10}$ and $X_{10}$ is phenyl, or $X_5$ is —$COOX_{10}$ and $X_{10}$ is t-butyl.

35. The taxane of claim 1 wherein $R_{10}$ is $R_{10a}OCOO$— and $R_{10a}$ is methyl or ethyl.

36. The taxane of claim 35 wherein $X_3$ is 2-furyl, 3-furyl, 2-thienyl, 3-thienyl, 2-pyridyl, 3-pyridyl or 4-pyridyl.

37. The taxane of claim 35 wherein $X_5$ is —$COX_{10}$ and $X_{10}$ is phenyl, or $X_5$ is —$COOX_{10}$ and $X_{10}$ is t-butyl.

38. The taxane of claim 35 wherein $R_{14}$ is hydrido.

39. The taxane of claim 38 wherein $X_3$ is 2-furyl, 3-furyl, 2-thienyl, 3-thienyl, 2-pyridyl, 3-pyridyl or 4-pyridyl.

40. The taxane of claim 38 wherein $X_5$ is —$COX_{10}$ and $X_{10}$ is phenyl, or $X_5$ is —$COOX_{10}$ and $X_{10}$ is t-butyl.

41. The taxane of claim 35 wherein $R_2$ is benzoyloxy.

42. The taxane of claim 41 wherein $X_3$ is 2-furyl, 3-furyl, 2-thienyl, 3-thienyl, 2-pyridyl, 3-pyridyl or 4-pyridyl.

43. The taxane of claim 41 wherein $X_5$ is —$COX_{10}$ and $X_{10}$ is phenyl, or $X_5$ is —$COOX_{10}$ and $X_{10}$ is t-butyl.

44. The taxane of claim 35 wherein $R_{14}$ is hydrido and $R_9$ is keto.

45. The taxane of claim 44 wherein $X_3$ is 2-furyl, 3-furyl, 2-thienyl, 3-thienyl, 2-pyridyl, 3-pyridyl or 4-pyridyl.

46. The taxane of claim 44 wherein $X_5$ is —$COX_{10}$ and $X_{10}$ is phenyl, or $X_5$ is —$COOX_{10}$ and $X_{10}$ is t-butyl.

47. The taxane of claim 35 wherein $R_2$ is benzoyloxy and $R_9$ is keto.

48. The taxane of claim 47 wherein $X_3$ is 2-furyl, 3-furyl, 2-thienyl, 3-thienyl, 2-pyridyl, 3-pyridyl or 4-pyridyl.

49. The taxane of claim 47 wherein $X_5$ is —$COX_{10}$ and $X_{10}$ is phenyl, or $X_5$ is —$COOX_{10}$ and $X_{10}$ is t-butyl.

50. The taxane of claim 35 wherein $R_{14}$ is hydrido and $R_2$ is benzoyloxy.

51. The taxane of claim 50 wherein $X_3$ is 2-furyl, 3-furyl, 2-thienyl, 3-thienyl, 2-pyridyl, 3-pyridyl or 4-pyridyl.

52. The taxane of claim 50 wherein $X_5$ is —$COX_{10}$ and $X_{10}$ is phenyl, or $X_5$ is —$COOX_{10}$ and $X_{10}$ is t-butyl.

53. The taxane of claim 35 wherein $R_{14}$ is hydrido, $R_9$ is keto, and $R_2$ is benzoyloxy.

54. The taxane of claim 53 wherein $X_3$ is 2-furyl, 3-furyl, 2-thienyl, 3-thienyl, 2-pyridyl, 3-pyridyl or 4-pyridyl.

55. The taxane of claim 53 wherein $X_5$ is —$COX_{10}$ and $X_{10}$ is phenyl, or $X_5$ is —$COOX_{10}$ and $X_{10}$ is t-butyl.

56. The taxane of claim 53 wherein $X_5$ is —$COOX_{10}$ and $X_{10}$ is t-butyl.

57. The taxane of claim 56 wherein $X_3$ is 2-furyl, 3-furyl, 2-thienyl, 3-thienyl, 2-pyridyl, 3-pyridyl or 4-pyridyl.

58. A taxane having the formula

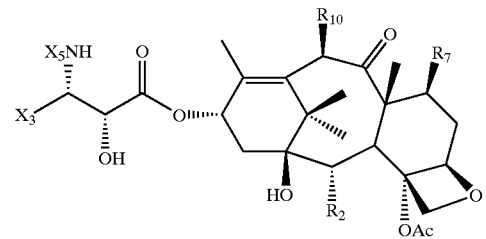

$R_2$ is benzoyloxy;

$R_7$ is hydroxy;

$R_{10}$ is $R_{10a}OCOO$—;

$X_3$ is substituted or unsubstituted heterocyclo;

$X_5$ is —$COX_{10}$, —$COOX_{10}$, or —$CONHX_{10}$;

$X_{10}$ is hydrocarbyl, substituted hydrocarbyl, or heterocyclo; and $R_{10a}$ is hydrocarbyl, substituted hydrocarbyl, or heterocyclo; and Ac is acetyl.

59. The taxane of claim 58 wherein $X_3$ is 2-furyl, 3-furyl, 2-thienyl, 3-thienyl, 2-pyridyl, 3-pyridyl or 4-pyridyl.

60. The taxane of claim 59 wherein $X_5$ is —$COX_{10}$ and $X_{10}$ is phenyl, or $X_5$ is —$COOX_{10}$ and $X_{10}$ is t-butyl.

61. The taxane of claim 58 wherein $X_3$ is furyl or thienyl.

62. The taxane of claim 61 wherein $X_5$ is —$COX_{10}$ and $X_{10}$ is substituted or unsubstituted phenyl, 2-furyl, 3-furyl, 2-thienyl, 3-thienyl, 2-pyridyl, 3-pyridyl, 4-pyridyl, $C_1$–$C_8$ alkyl, $C_2$–$C_8$ alkenyl, or $C_2$–$C_8$ alkynyl, or $X_5$ is —$COOX_{10}$ and $X_{10}$ is substituted or unsubstituted $C_1$–$C_8$ alkyl, $C_2$–$C_8$ alkenyl, or $C_2$–$C_8$ alkynyl.

63. The taxane of claim 61 wherein $X_5$ is —$COX_{10}$ and $X_{10}$ is phenyl, or $X_5$ is —$COOX_{10}$ and $X_{10}$ is t-butyl.

64. The taxane of claim 58 wherein $R_{10a}$ is methyl or ethyl.

65. The taxane of claim 64 wherein $X_3$ is 2-furyl, 3-furyl, 2-thienyl, 3-thienyl, 2-pyridyl, 3-pyridyl or 4-pyridyl.

66. The taxane of claim 65 wherein $X_5$ is —$COX_{10}$ and $X_{10}$ is substituted or unsubstituted phenyl, 2-furyl, 3-furyl, 2-thienyl, 3-thienyl, 2-pyridyl, 3-pyridyl, 4-pyridyl, $C_1$–$C_8$ alkyl, $C_2$–$C_8$ alkenyl, or $C_2$–$C_8$ alkynyl, or $X_5$ is —$COOX_{10}$ and $X_{10}$ is substituted or unsubstituted $C_1$–$C_8$ alkyl, $C_2$–$C_8$ alkenyl, or $C_2$–$C_8$ alkynyl.

67. The taxane of claim 65 wherein $X_5$ is —$COX_{10}$ and $X_{10}$ is phenyl, or $X_5$ is —$COOX_{10}$ and $X_{10}$ is t-butyl.

68. The taxane of claim 64 wherein $X_3$ is furyl or thienyl.

69. The taxane of claim 68 wherein $X_5$ is —$COX_{10}$ and $X_{10}$ is substituted or unsubstituted phenyl, 2-furyl, 3-furyl, 2-thienyl, 3-thienyl, 2-pyridyl, 3-pyridyl, 4-pyridyl, $C_1$–$C_8$ alkyl, $C_2$–$C_8$ alkenyl, or $C_2$–$C_8$ alkynyl, or $X_5$ is —$COOX_{10}$ and $X_{10}$ is substituted or unsubstituted $C_1$–$C_8$ alkyl, $C_2$–$C_8$ alkenyl, or $C_2$–$C_8$ alkynyl.

70. The taxane of claim 68 wherein $X_5$ is —$COX_{10}$ and $X_{10}$ is phenyl, or $X_5$ is —$COOX_{10}$ and $X_{10}$ is t-butyl.

71. The taxane of claim 58 wherein $X_3$ is furyl or thienyl, $R_{10a}$ is ethyl, and $X_5$ is —$COX_{10}$ and $X_{10}$ is phenyl, or $X_5$ is —$COOX_{10}$ and $X_{10}$ is t-butyl.

72. The taxane of claim 58 wherein $X_3$ is 2-furyl or 2-thienyl, $R_{10a}$ is ethyl, $X_5$ is —$COOX_{10}$ and $X_{10}$ is t-butyl.

73. A taxane having the formula

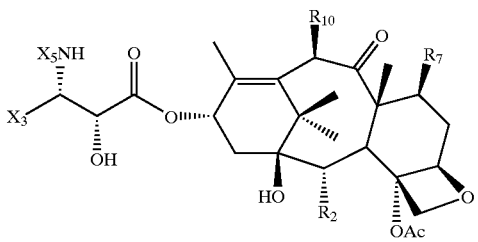

R$_2$ is benzoyloxy;
R$_7$ is hydroxy;
R$_{10}$ is R$_{10a}$OCOO—;
X$_3$ is heterocyclo;
X$_5$ is —COX$_{10}$, —COOX$_{10}$, or —CONHX$_{10}$;
X$_{10}$ is hydrocarbyl, substituted hydrocarbyl, or heterocyclo; and
R$_{10a}$ is alkyl, alkenyl, alkynyl, phenyl, or heterocyclo wherein alkyl comprises at least two carbon atoms; and
Ac is acetyl.

74. The taxane of claim 73 wherein X$_3$ is 2-furyl, 3-furyl, 2-thienyl, 3-thienyl, 2-pyridyl, 3-pyridyl or 4-pyridyl.

75. The taxane of claim 74 wherein X$_5$ is —COX$_{10}$ and X$_{10}$ is substituted or unsubstituted phenyl, 2-furyl, 3-furyl, 2-thienyl, 3-thienyl, 2-pyridyl, 3-pyridyl, 4-pyridyl, C$_1$–C$_8$ alkyl, C$_2$–C$_8$ alkenyl, or C$_2$–C$_8$ alkynyl, or X$_5$ is —COOX$_{10}$ and X$_{10}$ is substituted or unsubstituted C$_1$–C$_8$ alkyl, C$_2$–C$_8$ alkenyl, or C$_2$–C$_8$ alkynyl.

76. The taxane of claim 74 wherein X$_5$ is —COX$_{10}$ and X$_{10}$ is phenyl, or X$_5$ is —COOX$_{10}$ and X$_{10}$ is t-butyl.

77. The taxane of claim 73 wherein X$_3$ is furyl or thienyl.

78. The taxane of claim 77 wherein X$_5$ is —COX$_{10}$ and X$_{10}$ is substituted or unsubstituted phenyl, 2-furyl, 3-furyl, 2-thienyl, 3-thienyl, 2-pyridyl, 3-pyridyl, 4-pyridyl, C$_1$–C$_8$ alkyl, C$_2$–C$_8$ alkenyl, or C$_2$–C$_8$ alkynyl, or X$_5$ is —COOX$_{10}$ and X$_{10}$ substituted or unsubstituted C$_1$–C$_8$ alkyl, C$_2$–C$_8$ alkenyl, or C$_2$–C$_8$ alkynyl.

79. The taxane of claim 77 wherein X$_5$ is —COX$_{10}$ and X$_{10}$ is phenyl, or X$_5$ is —COOX$_{10}$ and X$_{10}$ is t-butyl.

80. The taxane of claim 73 wherein R$_{10a}$ is ethyl.

81. The taxane of claim 80 wherein X$_3$ is 2-furyl, 3-furyl, 2-thienyl, 3-thienyl, 2-pyridyl, 3-pyridyl or 4-pyridyl.

82. The taxane of claim 80 wherein X$_5$ is —COX$_{10}$ and X$_{10}$ is substituted or unsubstituted phenyl, 2-furyl, 3-furyl, 2-thienyl, 3-thienyl, 2-pyridyl, 3-pyridyl, 4-pyridyl, C$_1$–C$_8$ alkyl, C$_2$–C$_8$ alkenyl, or C$_2$–C$_8$ alkynyl, or X$_5$ is —COOX$_{10}$ and X$_{10}$ is substituted or unsubstituted C$_1$–C$_8$ alkyl, C$_2$–C$_8$ alkenyl, or C$_2$–C$_8$ alkynyl.

83. The taxane of claim 80 wherein X$_5$ is —COX$_{10}$ and X$_{10}$ is phenyl, or X$_5$ is —COOX$_{10}$ and X$_{10}$ is t-butyl.

84. The taxane of claim 80 wherein X$_3$ is furyl or thienyl.

85. The taxane of claim 84 wherein X$_5$ is —COX$_{10}$ and X$_{10}$ is substituted or unsubstituted phenyl, 2-furyl, 3-furyl, 2-thienyl, 3-thienyl, 2-pyridyl, 3-pyridyl, 4-pyridyl, C$_1$–C$_8$ alkyl, C$_2$–C$_8$ alkenyl, or C$_2$–C$_8$ alkynyl, or X$_5$ is —COOX$_{10}$ and X$_{10}$ is substituted or unsubstituted C$_1$–C$_8$ alkyl, C$_2$–C$_8$ alkenyl, or C$_2$–C$_8$ alkynyl.

86. The taxane of claim 84 wherein X$_5$ is —COX$_{10}$ and X$_{10}$ is phenyl, or X$_5$ is —COOX$_{10}$ and X$_{10}$ is t-butyl.

87. The taxane of claim 84 wherein X$_5$ is —COOX$_{10}$ and X$_{10}$ is t-butyl.

88. A pharmaceutical composition comprising the taxane of claim 1 and one or more pharmacologically acceptable, inert or physiologically active diluents or adjuvants.

89. The pharmaceutical composition of claim 88 wherein X$_3$ is 2-furyl, 3-furyl, 2-thienyl, 3-thienyl, 2-pyridyl, 3-pyridyl or 4-pyridyl.

90. The pharmaceutical composition of claim 89 wherein X$_5$ is —COX$_{10}$ and X$_{10}$ is substituted or unsubstituted phenyl, 2-furyl, 3-furyl, 2-thienyl, 3-thienyl, 2-pyridyl, 3-pyridyl, 4-pyridyl, C$_1$–C$_8$ alkyl, C$_2$–C$_8$ alkenyl, or C$_2$–C$_8$ alkynyl, or X$_5$ is —COOX$_{10}$ and X$_{10}$ is substituted or unsubstituted C$_1$–C$_8$ alkyl, C$_2$–C$_8$ alkenyl, or C$_2$–C$_8$ alkynyl.

91. The pharmaceutical composition of claim 89 wherein X$_5$ is —COX$_{10}$ and X$_{10}$ is phenyl, or X$_5$ is —COOX$_{10}$ and X$_{10}$ is t-butyl.

92. The pharmaceutical composition of claim 88 wherein R$_{10a}$ is methyl, ethyl or propyl.

93. The pharmaceutical composition of claim 92 wherein X$_3$ is 2-furyl, 3-furyl, 2-thienyl, 3-thienyl, 2-pyridyl, 3-pyridyl or 4-pyridyl.

94. The pharmaceutical composition of claim 93 wherein X$_5$ is —COX$_{10}$ and X$_{10}$ is substituted or unsubstituted phenyl, 2-furyl, 3-furyl, 2-thienyl, 3-thienyl, 2-pyridyl, 3-pyridyl, 4-pyridyl, C$_1$–C$_8$ alkyl, C$_2$–C$_8$ alkenyl, or C$_2$–C$_8$ alkynyl, or X$_5$ is —COOX$_{10}$ and X$_{10}$ is substituted or unsubstituted C$_1$–C$_8$ alkyl, C$_2$–C$_8$ alkenyl, or C$_2$–C$_8$ alkynyl.

95. The pharmaceutical composition of claim 93 wherein X$_5$ is —COX$_{10}$ and X$_{10}$ is phenyl, or X$_5$ is —COOX$_{10}$ and X$_{10}$ is t-butyl.

96. The pharmaceutical composition of claim 89 wherein X$_3$ is furyl or thienyl, R$_{10a}$ is methyl or ethyl, and X$_5$ is —COX$_{10}$ and X$_{10}$ is phenyl, or X$_5$ is —COOX$_{10}$ and X$_{10}$ is t-butyl.

97. The pharmaceutical composition of claim 89 wherein X$_3$ is substituted or unsubstituted furyl, R$_{10a}$ is methyl or ethyl, and X$_5$ is —COX$_{10}$ and X$_{10}$ is phenyl, or X$_5$ is —COOX$_{10}$ and X$_{10}$ is t-butyl.

98. The pharmaceutical composition of claim 89 wherein X$_3$ is substituted or unsubstituted thienyl, R$_{10a}$ is methyl or ethyl, and X$_5$ is —COX$_{10}$ and X$_{10}$ is phenyl, or X$_5$ is —COOX$_{10}$ and X$_{10}$ is t-butyl.

99. The pharmaceutical composition of claim 89 wherein X$_3$ is 2-furyl or 2-thienyl, R$_{10a}$ is methyl, X$_5$ is —COOX$_{10}$ and X$_{10}$ is t-butyl.

100. The pharmaceutical composition of claim 89 wherein X$_3$ is 2-furyl, R$_{10a}$ is ethyl, X$_5$ is —COOX$_{10}$ and X$_{10}$ is t-butyl.

101. The pharmaceutical composition of claim 89 wherein X$_3$ is 2-thienyl, R$_{10a}$ is ethyl, X$_5$ is —COOX$_{10}$ and X$_{10}$ is t-butyl.

102. A pharmaceutical composition comprising the taxane of claim 58 and one or more pharmacologically acceptable, inert or physiologically active diluents or adjuvants.

103. A pharmaceutical composition comprising the taxane of claim 61 and one or more pharmacologically acceptable, inert or physiologically active diluents or adjuvants.

104. A composition for oral administration comprising the taxane of claim 1 and at least one pharmaceutically acceptable carrier.

105. The composition of claim 104 wherein R$_{10}$ is R$_{10a}$OCOO— and R$_{10a}$ is substituted or unsubstituted C$_1$–C$_8$ alkyl, C$_2$–C$_8$ alkenyl or C$_2$–C$_8$ alkynyl.

106. The composition of claim 105 wherein X$_3$ is 2-furyl, 3-furyl, 2-thienyl, 3-thienyl, 2-pyridyl, 3-pyridyl or 4-pyridyl.

107. The composition of claim 106 wherein X$_5$ is —COX$_{10}$ and X$_{10}$ is phenyl, or X$_5$ is —COOX$_{10}$ and X$_{10}$ is t-butyl.

108. The composition of claim 107 wherein $R_{10a}$ is methyl, ethyl or propyl.

109. The pharmaceutical composition of claim 108 wherein $X_3$ is 2-furyl or 2-thienyl, $R_{10a}$ is ethyl, $X_5$ is —$COOX_{10}$ and $X_{10}$ is t-butyl.

110. A pharmaceutical composition comprising the taxane of claim 78 and at least one pharmaceutical acceptable carrier.

111. A method of inhibiting tumor growth in a mammal, said method comprising orally administering a therapeutically effective amount of a composition comprising the taxane of claim 104 and at least one pharmaceutically acceptable carrier.

112. The method of claim 111 wherein $R_{10}$ is $R_{10a}OCOO$— and $R_{10a}$ is substituted or unsubstituted $C_1$–$C_8$ alkyl, $C_2$–$C_8$ alkenyl or $C_2$–$C_8$ alkynyl.

113. The method of claim 112 wherein $X_3$ is 2-furyl, 3-furyl, 2-thienyl, 3-thienyl, 2-pyridyl, 3-pyridyl or 4-pyridyl.

114. The method of claim 113 herein $X_5$ is —$COX_{10}$ and $X_{10}$ is phenyl, or $X_5$ is —$COOX_{10}$ and $X_{10}$ is t-butyl.

115. The method of claim 114 wherein $R_{10a}$ is methyl, ethyl or propyl.

116. The method of claim 111 wherein $X_3$ is 2-furyl or 2-thienyl, $R_{10a}$ is ethyl, $X_5$ is —$COOX_{10}$ and $X_{10}$ is t-butyl.

117. A method of inhibiting tumor growth in a mammal, said method comprising orally administering a therapeutically effective amount of a composition comprising the taxane of claim 78 and at least one pharmaceutical acceptable carrier.

* * * * *

UNITED STATES PATENT AND TRADEMARK OFFICE
CERTIFICATE OF CORRECTION

PATENT NO. : 6,660,866 B2
DATED : December 9, 2003
INVENTOR(S) : Holton

It is certified that error appears in the above-identified patent and that said Letters Patent is hereby corrected as shown below:

Title page,
Item [*] Notice, delete the phrase "by 94 days" and insert -- by 49 days --

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,660,866 B2
DATED         : December 9, 2003
INVENTOR(S)   : Robert A. Holton It is certified that error appears in the above-identified patent and that said Letters Patent is hereby corrected as shown below:

Title page,
Item [73] Assignee, "PSU Research Foundation" should read -- FSU Research Foundation, Inc. --

Column 10,
Line 62, "dimethylacetamideamides," should read -- dimethylacetamide, --.

Column 19,
Line 37, "triethylsilyi-3'-" should read -- triethylsilyl-3'- --.

Column 23,
Line 66, that portion of the table reading "3PyCO-" should read -- 3-PyCO- --.

Column 26,
Line 53, that portion of the table reading "3PyCO-" should read -- 3-PyCO- --.

Column 29,
Line 34, that portion of the table reading "3PyCO-" should read -- 3-PyCO- --.

Column 45,
Line 39, "$X_{10}$ substituted" should read -- $X_{10}$ is substituted --.

Column 47,
Line 7, "pharmaceutical" should read -- pharmaceutically --.

UNITED STATES PATENT AND TRADEMARK OFFICE
CERTIFICATE OF CORRECTION

PATENT NO. : 6,660,866 B2
DATED : December 9, 2003
INVENTOR(S) : Robert A. Holton It is certified that error appears in the above-identified patent and that said Letters Patent is hereby corrected as shown below:

Column 48,
Line 4, "herein" should read -- wherein --.
Line 13, "pharmaceutical" should read -- pharmaceutically --.

Signed and Sealed this

Fifth Day of April, 2005

JON W. DUDAS
*Director of the United States Patent and Trademark Office*